United States Patent
Ziemer et al.

(10) Patent No.: US 6,251,827 B1
(45) Date of Patent: Jun. 26, 2001

(54) ACYLSULFAMOYLBENZAMIDES, CROP PROTECTION COMPOSITIONS COMPRISING THEM, AND PROCESSES FOR THEIR PREPARATION

(75) Inventors: Frank Ziemer, Kriftel; Lothar Willms, Hofheim; Thomas Auler, Kelsterbach; Hermann Bieringer, Eppstein; Christopher Rosinger, Hofheim, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/161,120

(22) Filed: Sep. 25, 1998

(51) Int. Cl.[7] ........................ A01N 43/40; A01N 37/10; A01N 47/40; C07D 213/08; C07D 213/06; C07D 401/00; C07D 211/70; C07D 211/72

(52) U.S. Cl. ........................ 504/130; 504/141; 504/144; 546/250; 546/251; 546/252; 546/268.1; 546/276.1; 546/279.1; 546/314; 546/315; 546/316; 546/317; 564/80; 564/86; 564/87

(58) Field of Search ....................... 504/116, 130, 504/141, 144; 564/80, 86, 87; 546/250, 251, 252, 268.1, 276.1, 279.1, 314, 315, 316, 317

(56) References Cited

U.S. PATENT DOCUMENTS

| | | |
|---|---|---|
| 5,428,046 | 6/1995 | Weidmann et al. . |
| 5,607,954 | 3/1997 | Weidmann et al. . |
| 5,620,996 | 4/1997 | Weidmann et al. . |

FOREIGN PATENT DOCUMENTS

| | | |
|---|---|---|
| 0562512 A1 | 9/1993 | (EP) . |
| 0567997 | 11/1993 | (EP) . |
| 0590520 A1 | 4/1994 | (EP) . |
| 0673932 A1 | 9/1995 | (EP) . |
| WO 96/10559 | 4/1996 | (WO) . |
| 93/2983 | 1/1994 | (ZA) . |
| 98/2983 | 1/1994 | (ZA) . |

OTHER PUBLICATIONS

Imai et al, Reaction of Ni–benzoylsaccharin with amines, Nippon Kagaku Kagaku Kaishi, vol. 1, 123–6, 1975.*
Chemical Abstracts No. XP 002092978.
Chemical Abstracts No. XP 002092977.
Chemical Abstracts No. XP 002092976.
Imai et al., 54972–81–5, Caplus, 1975, p. 40.

* cited by examiner

Primary Examiner—S. Mark Clardy
Assistant Examiner—Alton Pryor
(74) Attorney, Agent, or Firm—Frommer Lawrence & Haug LLP

(57) ABSTRACT

Acylsulfamoylbenzamides of the formula I and crop protection compositions comprising them are described. In this formula I, $R^1$, $R^2$, $R_3$, $R^4$ and $R^5$ are various organic radicals and X is CH or N.

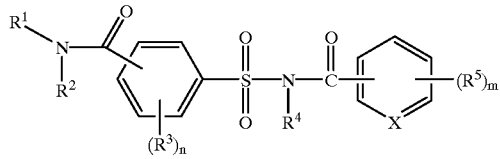

(I)

14 Claims, No Drawings

ACYLSULFAMOYLBENZAMIDES, CROP PROTECTION COMPOSITIONS COMPRISING THEM, AND PROCESSES FOR THEIR PREPARATION

The present invention relates to crop protection compositions which comprise acylsulfamoylbenzamides and, if appropriate, pesticides, and also to certain acylsulfamoylbenzamides and to processes for their preparation.

When controlling undesirable organisms in crops of plants which are useful for agriculture or forestry by using pesticides, the useful plants are frequently also damaged to a greater or lesser extent, in a manner which is undesirable per se, by the pesticides employed. This effect is encountered in particular with the use of a considerable number of herbicides in crops of useful plants such as maize, rice, or cereals, and there primarily in the post-emergence application. In some instances, the useful plants can be protected against the phytotoxic properties of the pesticides by employing safeners or antidotes, without adversely affecting the pesticidal activity against the harmful organisms.

Compounds which have hitherto been disclosed as safeners have various chemical structures. Thus, U.S. Pat. No. 4,902,340 discloses derivatives of quinolin-8-oxy-alkanoic acids as safeners for herbicides from the group of the diphenyl ethers and the pyridyloxyphenoxypropionic acids, and EP-A 0 520 371 discloses isoxazolines and isothiazolines as safeners for various kinds of herbicides, aryloxyphenoxycarboxylic acids, sulfonylureas and imidazolinones being mentioned as preferred herbicides in the latter publication.

In *Nippon Kagaku Kaishi*, 1975, 123–126, (*Chem. Abstr.*, (1976), 84: 17204), Imai et al. describe three acylsulfamoylbenzamides, in particular the compounds 2-(benzoylsulfamoyl)-N-phenylbenzamide
2-(benzoylsulfamoyl)-N-benzylbenzamide
4-(2-benzoylsulfamoylbenzoylamino)benzoic acid A particular biological activity or other properties of these compounds are not mentioned.

EP-A 0 562 512 discloses acylsulfamoylbenzamides which carry an aminocarbonyl group in position 2 or in position 6 of the pyridine ring. EP-A 0 590 520 discloses acylsulfamoylbenzamides which are optionally substituted in position 2 or in position 6 of the pyridine ring by an ester group. EP-A 0 673 932 mentions acylsulfamoylbenzamides which in each case carry an aminocarbonyl group in position 2 and position 4 of the pyridine ring. In these three publications, the acylsulfamoylbenzamides mentioned are described as medicaments for fibrotic diseases. A safener action of acylsulfamoylbenzamides has hitherto not been known.

When using safeners for protecting useful plants against damage by pesticides, it has been found that in many instances known safeners still have certain disadvantages. These include:
- the safener reduces the activity of the pesticides, in particular those of herbicides, against the harmful plants
- the crop-protecting properties are insufficient
- in combination with a given herbicide, the spectrum of the useful plants in which the safener/herbicide is to be employed is not sufficiently wide
- a given safener cannot be combined with a sufficiently large number of herbicides.

It is an object of the present invention to provide crop protection compositions comprising compounds having improved safener action and, optionally, pesticides.

This object is achieved by crop protection compositions comprising, optionally, one or more pesticides, which comprise at least one acylsulfamoylbenzamide of the formula I, if appropriate also in the form of its salt,

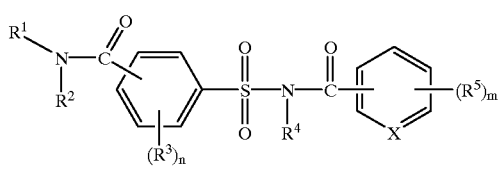

(I)

in which
x is CH or N;
$R^1$ is hydrogen, heterocyclyl or a hydrocarbon radical, where the two last-mentioned radicals are optionally substituted by one or more identical or different radicals selected from the group consisting of halogen, cyano, nitro, amino, hydroxyl, carboxyl, CHO, $CONH_2$, $SO_2NH_2$ and $Z^a$—$R^a$;
$R^2$ is hydrogen, hydroxyl, $(C_1–C_6)$-alkyl, $(C_2–C_6)$-alkenyl, $(C_2–C_6)$-alkynyl, $(C_1–C_6)$-alkoxy, $(C_2–C_6)$-alkenyloxy, where the five last-mentioned radicals are optionally substituted by one or more identical or different radicals selected from the group consisting of halogen, hydroxyl, $(C_1–C_4)$-alkyl, $(C_1–C_4)$-alkoxy and $(C_1–C_4)$-alkylthio, or
$R^1$ and $R^2$ together with the linking nitrogen atom form a 3- to 8-membered saturated or unsaturated ring;
$R^3$ is halogen, cyano, nitro, amino, hydroxyl, carboxyl, CHO, $CONH_2$, $SO_2NH_2$ or $Z^b$—$R^b$;
$R^4$ is hydrogen, $(C_1–C_4)$-alkyl, $(C_2–C_4)$-alkenyl or $(C_2–C_4)$-alkynyl;
$R^5$ is halogen, cyano, nitro, amino, hydroxyl, carboxyl, phosphoryl, CHO, $CONH_2$, $SO_2NH_2$ or $Z^c$—$R^c$;
$R^a$ is a $(C_2–C_{20})$-alkyl radical whose hydrocarbon chain is interrupted once or more than once by oxygen atoms, is heterocyclyl or a hydrocarbon radical, where the two last-mentioned radicals are optionally substituted by one or more identical or different radicals selected from the group consisting of halogen, cyano, nitro, amino, hydroxyl, mono- and di-$[(C_1–C_4)$-alkyl]amino;
$R^b$, $R^c$ independently of one another are a $(C_2–C_{20})$-alkyl radical whose hydrocarbon chain is interrupted once or more than once by oxygen atoms, are heterocyclyl or a hydrocarbon radical, where the two last-mentioned radicals are optionally substituted by one or more identical or different radicals selected from the group consisting of halogen, cyano, nitro, amino, hydroxyl, phosphoryl, $(C_1–C_4)$-haloalkoxy, mono- and di-$[(C_1–C_4)$-alkyl]amino;
$Z^a$ is a divalent unit selected from the group consisting of O, S, CO, CS, C(O)O, C(O)S, SO, $SO_2$, $NR^d$, $C(O)NR^d$ or $SO_2NR^d$;
$Z^b$, $Z^c$ independently of one another are a direct bond or a divalent unit selected from the group consisting of O, S, CO, CS, C(O)O, C(O)S, SO, $SO_2$, $NR^d$, $SO_2NR^d$ or $C(O)NR^d$;
$R^d$ is hydrogen, $(C_1–C_4)$-alkyl or $(C_1–C_4)$-haloalkyl;
n is an integer from 0 to 4 and
m, in the case that X is CH, is an integer from 0 to 5, and, in the case that X is N, is an integer from 0 to 4.

The terms mentioned hereinabove and hereinbelow have the meanings outlined below:

The term "halogen" includes fluorine, chlorine, bromine and iodine.

The term "$(C_1-C_4)$-alkyl" is to be understood as a straight-chain or branched hydrocarbon radical having 1, 2, 3 or 4 carbon atoms, for example the methyl, ethyl, propyl, isopropyl, 1-butyl, 2-butyl, 2-methylpropyl or tert-butyl radical. Correspondingly, alkyl radicals having a greater range of carbon atoms are to be understood as straight-chain or branched saturated hydrocarbon radicals which contain a number of carbon atoms which corresponds to this range. The term "$(C_1-C_6)$-alkyl" thus includes the abovementioned alkyl radicals, and also, for example, the pentyl, 2-methylbutyl, 1, 1-dimethylpropyl and hexyl radical.

If the carbon chain of an alkyl radical is interrupted by more than one oxygen atoms, this means that two oxygen atoms are at no time directly adjacent.

"$(C_1-C_4)$-haloalkyl" is to be understood as an alkyl group mentioned under the term "$(C_1-C_4)$-alkyl" in which one or more hydrogen atoms are replaced by the corresponding number of identical or different halogen atoms, preferably chlorine or fluorine, such as the trifluoromethyl, the 1-fluoroethyl, the 2,2,2-trifluoroethyl, the chloromethyl, fluoromethyl, the difluoromethyl and the 1,1,2,2-tetrafluoroethyl group.

"$(C_1-C_4)$-alkoxy" is to be understood as an alkoxy group whose hydrocarbon radical has the meaning given under the term "$(C_1-C_4)$-alkyl". Alkoxy groups embracing a larger range of carbon atoms are to be understood likewise.

The terms "alkenyl" and "alkynyl" having a prefix stating a range of carbon atoms denote a straight-chain or branched hydrocarbon radical having a number of carbon atoms corresponding to this range, this hydrocarbon radical having at least one multiple bond which can be in any position of the unsaturated radical in question. "$(C_2-C_6)$-alkenyl" thus denotes, for example, the vinyl, allyl, 2-methyl-2-propenyl, 2-butenyl, pentenyl, 2-methylpentenyl or the hexenyl group. "$(C_2-C_6)$-alkynyl" denotes, for example, the ethinyl, propargyl, 2-methyl-2-propinyl, 2-butinyl, 2-pentinyl and the 2-hexinyl group.

"$(C_3-C_8)$-cycloalkyl" denotes monocyclic alkyl radicals, such as the cyclopropyl, cyclobutyl, cyclopentyl, cyclohexyl, cycloheptyl or cyclooctyl radical and bicyclic alkyl radicals, such as the norbornyl radical.

"$(C_3-C_8)$-cycloalkoxy" or "$(C_3-C_8)$-cycloalkylthio" is to be understood as one of the abovementioned $(C_3-C_8)$-cycloalkyl radicals which is attached via an oxygen or sulfur atom.

"$(C_1-C_6)$-alkylthio" is an alkylthio group whose hydrocarbon radical has the meaning given under the term "$(C_1-C_6)$-alkyl". Correspondingly, "$(C_1-C_8)$-alkylsulfinyl" is, for example, the methyl-, ethyl-, propyl-, isopropyl-, butyl-, isobutyl-, sec-butyl- or tert-butylsulfinyl group and "$(C_1-C_6)$-alkylsulfonyl" is, for example, the methyl-, ethyl-, propyl-, isopropyl-, butyl-, isobutyl-, sec-butyl- and tert-butylsulfonyl group.

"Mono- and di-[$(C_1-C_4)$-alkyl]amino" is a nitrogen atom which is substituted by one or two identical or different alkyl radicals of the above definition. Other composite terms, such as $(C_3-C_6)$-Cycloalkenyl and [$(C_1-C_6)$-alkylthio]carbonyl are to be understood correspondingly, in accordance with the above definitions.

The term "aryl" is to be understood as an isocyclic, mono-, bi- or polycyclic aromatic radical preferably having 6 to 14, in particular 6 to 12, carbon atoms, such as phenyl, naphthyl or biphenylyl, preferably phenyl.

The term "heterocyclyl" denotes a mono- or bicyclic radical which is fully saturated, partially or fully unsaturated and which contains one to five identical or different atoms selected from the group consisting of nitrogen, sulfur and oxygen, where, however, two oxygen atoms may not be directly adjacent and at least one carbon atom must be present in the ring, for example a thiophene, furan, pyrrol, thiazol, oxazol, imidazol, isothiazol, isoxazol, pyrazol, 1,3,4-oxadiazol, 1,3,4-thiadiazol, 1,3,4-triazol, 1,2,4-oxadiazol, 1,2,4-thiadiazol, 1,2,4-triazol, 1,2,3-triazol, 1,2,3,4-tetrazol, benzo[b]thiophen, benzo[b]furan, indol, benzo[c]thiophen, benzo[c]furan, isoindol, benzoxazol, benzothiazol, benzimidazol, benzisoxazol, benzisothiazol, benzopyrazol, benzothiadiazol, benzotriazol, dibenzofuran, dibenzothiophen, carbazol, pyridine, pyrazin, pyrimidine, pyridazin, 1,3,5-triazin, 1,2,4-triazin, 1,2,4,5-tetrazin, quinolin, isoquinolin, quinoxalin, quinazolin, quinolin, 1,8-naphthyridin, 1,5-naphthyridin, 1,6-naphthyridin, 1,7-naphthyridin, phthalazin, pyridopyrimidin, purin, pteridin, piperidine, pyrrolidine, oxazolin, tetrahydrofuran, tetrahydropyran, isoxazolidin or thiazolidin radical.

A "hydrocarbon radical" is a straight-chain, branched or cyclic hydrocarbon radical which may be saturated, partially saturated, unsaturated or aromatic, for example alkyl, alkenyl, alkynyl, cycloalkyl, cycloalkenyl and aryl, preferably alkyl, alkenyl and alkynyl having up to 20 carbon atoms or cycloalkyl having 3 to 6 ring atoms or phenyl.

In the cases where two or more radicals $R^3$ and/or $R^5$ are present at a benzene or pyridine ring, i.e. if m and/or n are greater than one, these radicals may in each case be identical or different.

If $R^1$ in the formula I is a hydrocarbon radical, this hydrocarbon radical has preferably up to 20 carbon atoms. If this hydrocarbon radical carries further carbon-containing substituents, the total number of all carbon atoms of this radical $R^1$ is preferably 2 to 30.

In the case where $Z^a$, $Z^b$ and/or $Z^c$ are a divalent unit which is unsymmetrical, i.e. which allows two possibilities of attachment, in each case both possibilities of attachment of $Z^a$, $Z^b$, $Z^c$ with $R^a$, $R^b$, $R^c$ on the one hand and the remainder of the molecule on the other hand are embraced by the formula I.

Depending on the kind and the linkage of the substituents, the compounds of formula I may be present as stereoisomers. If, for example, one or more alkenyl groups are present, diastereomers may occur. If, for example, one or more asymmetric carbon atoms are present, enantiomers and diastereomers may occur. Stereoisomers can be obtained from the mixtures which are obtained in the preparation by customary separation methods, for example by chromatographic separation processes. It is also possible to prepare stereoisomers selectively by employing stereoselective reactions using optically active starting materials and/or auxiliaries. The invention thus also relates to all stereoisomers and mixtures thereof which are embraced by the formula I but not specifically defined.

The possibilities of combining the various substituents of formula I are to be understood in such a way that the general principles of the synthesis of chemical compounds are to be observed, i.e. that no compounds are to be formed of which the skilled worker knows that they are chemically unstable or impossible.

The compounds of the formula I can form salts. Salt formation may occur by action of a base on those compounds of the formula I which carry an acidic hydrogen atom, for example in the case of $R^4$=H or $R^5$=COOH. Suitable bases are, for example, organic amines and also ammonium, alkali metal or alkaline earth metal hydroxides, carbonates and bicarbonates, in particular sodium hydroxide and potassium hydroxide, sodium carbonate and potassium carbonate and sodium bicarbonate and potassium bicarbonate. Salt formation can also occur by addition of an acid to basic groups, such as amino and alkylamino. Acids which are suitable for this purpose are inorganic and organic acids, for example HCl, HBr, $H_2SO_4$, $HNO_3$ and acetic acid.

In the crop protection compositions, those compounds of the formula I are most interesting in which $R^1$ is hydrogen, 3- to 8-membered heterocyclyl having up to three identical or different hetero atoms selected from the group consisting of nitrogen, oxygen and sulfur, $(C_1-C_{12})$-alkyl, $(C_2-C_8)$-alkenyl, $(C_2-C_8)$-alkynyl, $(C_3-C_8)$-cycloalkyl, $(C_3-C_8)$-Cycloalkenyl or aryl, where the seven last-mentioned radicals are optionally substituted by one or more identical or different radicals selected from the group consisting of halogen, cyano, nitro, amino, hydroxyl, carboxyl, $CHO$, $CONH_2$, $SO_2NH_2$ and $Z^a$—$R^a$;

$R^5$ is halogen, cyano, nitro, amino, hydroxyl, carboxyl, $CHO$, $CONH_2$, $SO_2NH_2$ or $Z^c$—$R^c$;

$R^a$ is a $(C_2-C_{12})$-alkyl radical whose hydrocarbon chain is interrupted once or more than once by oxygen atoms, is $(C_1-C_8)$-alkyl, $(C_3-C_6)$-cycloalkyl, $(C_2-C_8)$-alkenyl, $(C_3-C_6)$-cycloalkenyl, $(C_2-C_8)$-alkynyl, phenyl or 3- to 6-membered heterocyclyl having up to three identical or different hetero atoms selected from the group consisting of nitrogen, oxygen and sulfur, where the seven last-mentioned radicals independently of one another are optionally substituted by one or more identical or different radicals selected from the group consisting of halogen, cyano, nitro, amino, hydroxyl, mono- and di-$[(C_1-C_4)$-alkyl]amino;

$R^b$, $R^c$ independently of one another are a $(C_2-C_{12})$-alkyl radical whose hydrocarbon chain is interrupted once or more than once by oxygen atoms, is $(C_1-C_8)$-alkyl, $(C_3-C_6)$-cycloalkyl, $(C_2-C_8)$-alkenyl, $(C_3-C_6)$-Cycloalkenyl, $(C_2-C_8)$-alkynyl, phenyl or 3- to 6-membered heterocyclyl having up to three identical or different hetero atoms selected from the group consisting of N, O and S, where the seven last-mentioned radicals independently of one another are optionally substituted by one or more identical or different radicals selected from the group consisting of halogen, cyano, nitro, amino, hydroxyl, phosphoryl, $(C_1-C_4)$-haloalkoxy, mono and di-$[(C_1-C_4)$-alkyl]amino;

$Z^a$ is a divalent unit selected from the group consisting of O, S, CO, CS, C(O)O, C(O)S, SO, $SO_2$, $NR^d$ or $C(O)NR^d$;

$Z^b$, $Z^c$ independently of one another are a direct bond or a divalent unit selected from the group consisting of O, S, CO, CS, C(O)O, C(O)S, SO, $SO_2$, $NR^d$, $SO_2NR^d$ or $C(O)NR^d$ and $R^d$ is hydrogen, $(C_1-C_4)$-alkyl or $(C_1-C_4)$-haloalkyl.

Of particular interest in the crop protection compositions are those compounds of the formula I in which $R^1$ is hydrogen, $(C_1-C_8)$-alkyl, $(C_2-C_6)$-alkenyl, $(C_2-C_6)$-alkynyl, $(C_3-C_6)$-cycloalkyl, $(C_5-C_6)$-cycloalkenyl, phenyl or 3- to 6-membered heterocyclyl having up to three hetero atoms selected from the group consisting of nitrogen, oxygen and sulfur, where the seven last-mentioned radicals are optionally substituted by one or more identical or different substituents selected from the group consisting of halogen, cyano, $(C_1-C_6)$-alkoxy, $(C_1-C_6)$-alkylthio, $(C_1-C_4)$-alkylsulfinyl, $(C_1-C_4)$-alkylsulfonyl, $(C_2-C_4)$-alkenyloxy, $(C_2-C_4)$-alkenylthio, $(C_2-C_4)$-alkynyloxy, $(C_2-C_4)$-alkynylthio, $(C_3-C_6)$-cycloalkyl, $(C_5-C_6)$-cycloalkenyl, $(C_3-C_6)$-cycloalkoxy, $(C_5-C_6)$-cycloalkenyloxy, mono- and di$[(C_1-C_4)$-alkyl]amino, $[(C_1-C_6)$-alkoxy]carbonyl, $[(C_1-C_6)$-alkylthio]carbonyl, $[(C_1-C_6)$-alkyl]carbonyl, phenyl, phenyl-$(C_1-C_4)$alkoxy, 5- to 6-membered heterocyclyl having up to three hetero atoms selected from the group consisting of nitrogen, oxygen and sulfur and, in the case of cyclic radicals, also by $(C_1-C_4)$alkyl, where the twenty last-mentioned radicals are optionally substituted by one or more identical or different substituents selected from the group consisting of halogen and cyano and, in the case of cyclic radicals, also by $(C_1-C_4)$alkyl;

$R^3$, $R^5$ independently of one another are halogen, nitro, amino, hydroxyl, cyano, $SO_2NH_2$, $(C_1-C_6)$-alkyl, $(C_3-C_6)$-cycloalkyl, $(C_2-C_6)$-alkenyl, $(C_2-C_6)$-alkynyl, $(C_1-C_6)$-alkoxy, $(C_2-C_6)$-alkenyloxy, $(C_2-C_6)$-alkynyloxy, mono- and di-$[(C_1-C_4)$-alkyl]-aminosulfonyl, $(C_1-C_6)$-alkylthio, $(C_1-C_6)$-alkylsulfinyl, $(C_1-C_6)$-alkylsulfonyl, $(C_1-C_6)$-alkoxycarbonyl, $(C_1-C_6)$-alkylthiocarbonyl, $(C_1-C_6)$-alkylcarbonyl, where the fifteen last-mentioned radicals are optionally substituted by one or more identical or different radicals selected from the group consisting of halogen, $(C_1-C_4)$-haloalkoxy, cyano, $(C_1-C_6)$-alkoxy and, in the case of cyclic radicals, also by $(C_1-C_4)$-alkyl and $(C_1-C_4)$-haloalkyl.

In the crop protection compositions, those compounds of the formula I are preferred in which X is CH;

$R^1$ is hydrogen, $(C_1-C_6)$-alkyl, $(C_3-C_6)$-cycloalkyl, $(C_2-C_6)$-alkenyl, $(C_5-C_6)$-cycloalkenyl, phenyl or 3- to 6-membered heterocyclyl having up to three hetero atoms selected from the group consisting of nitrogen, oxygen and sulfur, where the six last-mentioned radicals are optionally substituted by one or more identical or different substituents selected from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also by $(C_1-C_4)$-alkyl and $(C_1-C_4)$-haloalkyl;

$R^2$ is hydrogen, $(C_1-C_6)$-alkyl, $(C_2-C_6)$-alkenyl, $(C_2-C_6)$-alkynyl, where the three last-mentioned radicals are optionally substituted by one or more identical or different substituents selected from the group consisting of halogen, hydroxyl, $(C_1-C_4)$-alkyl, $(C_1-C_4)$-alkoxy and $(C_1-C_4)$-alkylthio;

$R^3$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;

$R^4$ is hydrogen;

$R^5$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;

n is 0, 1 or 2 and m is 1 or 2.

Particularly preferred in the crop protection compositions are those compounds of the formula I in which $R^1$ is hydrogen, $(C_1-C_6)$-alkyl, $(C_3-C_6)$-cycloalkyl, where the two last-mentioned radicals are optionally substituted by one or more identical or different substituents selected from the group consisting of halogen, ($C_1$–$C_4$)-alkoxy, ($C_1$–$C_6$)-haloalkoxy and ($C_1$–$C_4$)-alkylthio and, in the case of cyclic radicals, also by ($C_1$–$C_4$)-alkyl and ($C_1$–$C_4$)-haloalkyl.

In the crop protection compositions, those compounds of the formula I are very particularly preferred in which the sulfamoyl group is in position 4 of the phenyl ring.

The compositions according to the invention may contain one or more pesticides. Suitable pesticides are, for example, herbicides, insecticides, fungicides, acaricides and nematicides which in each case, when used on their own, would cause phytotoxic damage to the crop plants or which would be likely to cause damage. Of particular interest are such pesticidally active compounds from the groups of the herbicides and insecticides, in particular herbicides.

Preference is given to crop protection compositions which comprise at least one herbicide and at least one compound of the formula I.

If the compositions according to the invention comprise pesticides, these compositions are, after appropriate dilution, applied either directly to the area under cultivation, to the already germinated harmful and/or useful plants or to the already emerged harmful and/or useful plants. If the compositions according to the invention do not comprise any pesticide, these compositions can be employed by the tank mix method—i.e. the user mixes and dilutes the agent which is protecting the useful plants and the pesticide, which are products which are separately commercially available, immediately prior to application to the area to be treated, or prior to the application of a pesticide, or after the application of a pesticide, or for the pretreatment of seed, i.e. for dressing the seed of the useful plants.

The joint application of safener and pesticide, in particular that of safener and herbicide as a ready-o-use formulation or the application by the tank mix method, is preferred.

For joint application with pesticides, the compounds of the formula I according to the invention can be applied simultaneously or in any order with the active compounds, in which case they are capable of reducing or eliminating altogether harmful side effects of these active compounds in crop plants, without adversely affecting the efficacy of these active compounds against undesirable harmful organisms. Damage which is caused by using a plurality of pesticides, for example by a plurality of herbicides or by herbicides in combination with insecticides or fungicides, can be reduced significantly or eliminated altogether. Thus, the area of application of conventional pesticides can be widened very considerably.

Insecticides which, on their own or together with herbicides, can cause damage to plants include, for example:

organophosphates, for example terbufos (Counter®), fonofos (Dyfonate®), phorate (Thimet®), chlorpyriphos (Reldan®), carbamates, such as carbofuran (Furadan®), pyrethroid insecticides, such as tefluthrin (Force®), deltamethrin (Decis®) and tralomethrin (Scout®) and other insecticidal agents having a different mechanism of action.

Herbicides whose phytotoxic side effects on crop plants can be reduced using compounds of the formula I are, for example, herbicides from the group of the carbamates, thiocarbamates, haloacetanilides, substituted phenoxy-, naphthoxy- and phenoxyphenoxy carboxylic acid derivatives and heteroaryloxyphenoxyalkane carboxylic acid derivatives, such as quinolyloxy-, quinoxalyloxy-, pyridyloxy-, benzoxazolyloxy- and benzothiazolyloxyphenoxyalkane carboxylic acid esters, cyclohexanedione derivatives, imidazolinones, pyrimidinyloxypyridincarboxylic acid derivatives, pyrimidyloxybenzoic acid derivatives, sulfonylureas, triazolopyrimidinesulfonamide derivatives and S-(N-aryl-N-alkylcarbamoylmethyl) dithiophosphoric esters. Preference is given to phenoxyphenoxy- and heteroaryloxyphenoxy carboxylic acid esters and salts, sulfonylureas, imidazolinones and herbicides which, together with ALS inhibitors (acetolactate synthetase inhibitors), are employed for widening the activity spectrum, for example bentazone, cyanazin, atrazin, bromoxynil, dicamba and other leaf-acting herbicides.

Herbicides which are suitable for combination with the safeners according to the invention include, for example:

A) herbicides of the type of the phenoxyphenoxy- and heteroaryloxyphenoxycarboxylic acid derivatives, such as A1) phenoxyphenoxy- and benzyloxyphenoxycarboxylic acid derivatives, for example methyl 2-(4-(2,4-dichlorophenoxy)phenoxy)propionate (diclofop-methyl), methyl 2-(4-(4-bromo-2-chlorophenoxy)phenoxy)propionate (DE-A 26 01 548), methyl 2-(4-(4-bromo-2-fluorophenoxy)phenoxy)propionate (U.S. Pat. No. 4,808,750), methyl 2-(4-(2-chloro4-trifluoromethylphenoxy)phenoxy)propionate (DE-A 24 33 067), methyl 2-(4-(2-fluoro4-trifluoromethylphenoxy)phenoxy)propionate (U.S. Pat. No. 4,808,750), methyl 2-(4-(2,4-dichlorobenzyl)phenoxy)propionate (DE-A 24 17 487), ethyl 4-(4-(4-trifluoromethylphenoxy)phenoxy)pent-2-enoate, methyl 2-(4-(4-trifluoromethylphenoxy)phenoxy)propionate (DE-A 24 33 067);

A2) "mononuclear" heteroaryloxyphenoxyalkanecarboxylic acid derivatives, for example ethyl 2-(4-(3,5-dichloropyridyl-2-oxy)phenoxy)propionate (EP-A 0 002 925), propargyl 2-(4-(3,5-dichloropyridyl-2-oxy)phenoxy)propionate (EP-A 0 003 114), methyl 2-(4-(3-chloro-5-trifluoromethyl-2-pyridyloxy)phenoxy)propionate-methylester (EP-A 0 003 890), ethyl 2-(4-(3-chloro-5-trifluoromethyl-2-pyridyloxy)phenoxy)propionate (EP-A 0 003 890), propargyl 2-(4-(5-chloro-3-fluoro-2-pyridyloxy)phenoxy)propionate (EP-A 0 191 736), butyl 2-(4-(5-trifluoromethyl-2-pyridyloxy)phenoxy)propionate (Fluazifop-butyl);

A3) "dinuclear" heteroaryloxyphenoxyalkanecarboxylic acid derivatives, for example methyl and ethyl 2-(4-(6-chloro-2-quinoxalyloxy)phenoxy)propionate (quizalofop-methyl and quizalofop-ethyl), methyl 2-(4-(6-fluoro-2-quinoxalyloxy)phenoxy)propionate (see J. Pest. Sci. Vol. 10, 61 (1985)), 2-isopropylideneaminooxyethyl 2-(4-(6chloro-2-quinoxalyloxy)phenoxy)propionate (propaquizafop), ethyl 2-(4-(6-chlorobenzoxazol-2-yl-oxy)phenoxy) propionate (fenoxaprop-ethyl), its D(+) isomer (fenoxaprop-P-ethyl) and ethyl 2-(4-(6-chlorobenzothiazol-2-yloxy) phenoxy)propionate (DE-A 26 40 730), tetrahydro-2-furylmethyl 2-(4-(6-chloroquinoxalyloxy)phenoxy) propionate (EP-A 0 323 727);

B) herbicides from the group of the sulfonylureas, such as pyrimidine- or triazinylaminocarbonyl-[benzene-, pyridine-, pyrazol-, thiophen- and (alkylsulfonyl)alkylamino-] sulfamides. Preferred substituents at the pyrimidine ring or the triazine ring are alkoxy, alkyl, haloalkoxy, haloalkyl, halogen or dimethylamino, and it is possible to combine all substituents independently of one another. Preferred substituents in the benzene, pyridine, pyrazol, thiophene or (alkylsulfonyl)alkylamino moiety are alkyl, alkoxy, halogen, nitro, alkoxycarbonyl, aminocarbonyl, alkylaminocarbonyl, dialkylaminocarbonyl, alkoxyaminocarbonyl, haloalkoxy, haloalkyl, alkylcarbonyl, alkoxyalkyl, (alkanesulfonyl)alkylamino. Such suitable sulfonylureas are, for example, B1) phenyl- and benzylsulfonylureas and related compounds, for example 1-(2-chlorophenylsulfonyl)-3-(4-methoxy-6-methyl-1,3,5-triazin-2-yl)urea (chlorsulfuron), 1-(2-ethoxycarbonylphenylsulfonyl)-3-(4-chloro-6-methoxypyrimidin-2-yl)urea (chlorimuron-ethyl), 1-(2-methoxyphenylsulfonyl)-3-(4-methoxy-6-methyl-1,3,5-triazin-2-yl)urea (metsulfuron-methyl), 1-(2-chloroethoxyphenylsulfonyl)-3-(4-methoxy-6-methyl-1,3,5-triazin-2-yl)urea (triasulfuron), 1-(2-methoxycarbonylphenylsulfonyl)-3-(4,6-dimethylpyrimidin-2-yl)urea (sulfumeturon-methyl), 1-(2-methoxycarbonylphenylsulfonyl)-3-(4-methoxy-6-methyl-1,3,5-triazin-2-yl)-3-methylurea (tribenuron-methyl), 1-(2-methoxycarbonylbenzylsulfonyl)-3-(4,6-dimethoxypyrimidin-2-yl)urea (bensulfuron-methyl), 1-(2-methoxycarbonylphenylsulfonyl)-3-(4,6-bis-(difluoromethoxy)pyrimidin-2-yl)urea, (primisulfuron-methyl), 3-(4-ethyl-6-methoxy-1,3,5-triazin-2-yl)-1-(2,3-dihydro-1,1-dioxo-2-methylbenzo[b]thiophen-7-sulfonyl)urea (EP-A 0 796 83), 3-(4-ethoxy-6-ethyl-1,3,5-triazin-2-yl)-1-(2,3-dihydro-1,1-dioxo-2-methylbenzo[b]thiophen-7-sulfonyl)urea (EP-A 0 079 683), 3-(4-methoxy-6-methyl-1,3,5-triazin-2-yl)-1-(2-methoxycarbonyl-5-iodophenylsulfonyl)urea (WO 92/13845), DPX-66037, triflusulfuron-methyl (see Brighton Crop Prot. Conf.—Weeds—1995, p. 853), CGA-277476, (see Brighton Crop Prot. Conf.—Weeds—1995, p. 79), Methyl-2-[3-(4,6-dimethoxypyrimidin-2-yl)ureidosulfonyl]-4-methanesulfonamidomethylbenzoate (WO 95/10507), N,N-dimethyl-2-[3-(4,6-dimethoxypyrimidin-2-yl)ureidosulfonyl]-4-formylaminobenzamide (WO 95/01344);

B2) thienylsulfonylureas, for example 1-(2-methoxycarbonylthiophen-3-yl)-3-(4-methoxy4-methyl-1,3,5-triazin-2-yl)urea (thifensulfuron-methyl);

B3) pyrazolylsulfonylureas, for example 1-(4-ethoxycarbonyl-1-methylpyrazol-5-ylsulfonyl)-3-(4,6-dimethoxypyrimidin-2-yl)urea (pyrazosulfuron-methyl); methyl 3-chloro-5-(4,6-dimethoxypyrimidin-2-ylcarbamoylsulfamoyl)-1-methylpyrazol-4-arboxylate (EP-A 0 282 613); methyl 5-(4,6-dimethylpyrimidin-2-ylcarbamoylsulfamoyl)-1-(2-pyridyl)pyrazol-4-arboxylate (NC-330, see Brighton Crop Prot. Conference 'Weeds' 1991, Vol.1, p. 45 ff.), DPX-A8947, azimsulfuron, (see Brighton Crop Prot. Conf. 'Weeds' 1995, p. 65);

B4) sulfonediamide derivatives, for example 3-(4,6dimethoxypyrimidin-2-yl)-1-(N-methyl-N-methylsulfonylaminosulfonyl)urea (amidosulfuron) and its structural analogs (EP-A 0 131 258 and Z. Pfl. Krankh. Pfl. Schutz, special issue XII, 489–497 (1990));

B5) pyridylsulfonylureas, for example 1-(3-N,N-dimethylaminocarbonylpyridin-2-ylsulfonyl)-3-(4,6-dimethoxypyrimidin-2-yl)urea (nicosulfuron), 1-(3-ethylsulfonylpyridin-2-ylsulfonyl)-3-(4,6-dimethoxypyrimidin-2-yl)urea (rimsulfuron), methyl 2-[3-(4,6-dimethoxypyrimidin-2-yl)ureidosulfonyl]-6-trifluoromethyl-3-pyridincarboxylate, sodium salt (DPX-KE 459, flupyrsulfuron, see Brighton Crop Prot. Conf. Weeds, 1995, p. 49), pyridylsulfonylureas, as described in DE-A 40 00 503 and DE-A 40 30 577, preferably those of the formula

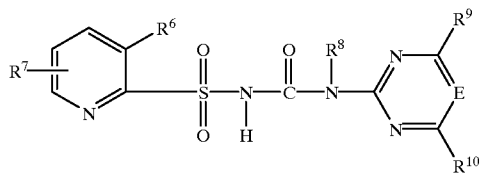

in which

E is CH or N, preferably CH, $R^6$ is iodine or $NR^{11}R^{12}$, $R^7$ is hydrogen, halogen, cyano, $(C_1-C_3)$-alkyl, $(C_1-C_3)$-alkoxy, $(C_1-C_3)$- haloalkyl, $(C_1-C_3)$-haloalkoxy, $(C_1-C_3)$-alkylthio, $(C_1-C_3)$-alkoxy-$(C_1-C_3)$-alkyl, $(C_1-C_3)$-alkoxycarbonyl, mono- or di-$(C_1-C_3)$-alkyl) amino, $(C_1-C_3)$-alkylsulfinyl or —sulfonyl, $SO_2$—$NR^aR^b$ or CO—$NR^aR^b$, in particular hydrogen, $R^a$ and $R^b$ independently of one another are hydrogen, $(C_1-C_3)$-akyl, $(C_1-C_3)$-alkenyl, $(C_1-C_3)$-alkynyl or together are —$(CH_2)_4$—, —$(CH_2)_5$—or —$(CH_2)_2$—O—$(CH_2)_2$—, $R^8$ is hydrogen or $CH_3$, $R^9$ is halogen, $(C_1-C_2)$-alkyl, $(C_1-C_2)$-alkoxy, $(C_1-C_2)$-haloalkyl, in particular $CF_3$, $(C_1-C_2)$-haloalkoxy, preferably $OCHF_2$ or $OCH_2CF_3$, $R^{10}$ is $(C_1-C_2)$-alkyl, $(C_1-C_2)$-haloalkoxy, preferably $OCHF_2$, or $(C_1-C_2)$-alkoxy, and $R^{11}$ is $(C_1-C_4)$-alkyl and $R^{12}$ is $(C_1-C_4)$-alkylsulfonyl or $R^{11}$ and $R^{12}$ together are a chain of the formula —$(CH_2)_3SO_2$—or —$(CH_2)_4SO_2$—, for example 3-4,6-dimethoxypyrimiden-2-yl)-1-(3-N-methylsulfonyl-N-methylaminopyridin-2-yl)sulfonylurea, or salts thereof;

B6) alkoxyphenoxysulfonylureas as described in EP-A 0 342 569, preferably those of the formula

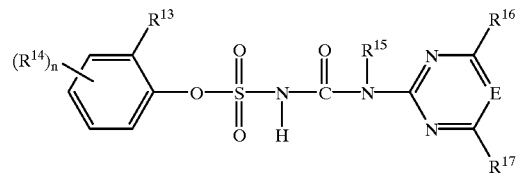

in which

E is CH or N, preferably CH, $R^{13}$ is ethoxy, propoxy or isopropoxy, $R^{14}$ is hydrogen, halogen, $NO_2$, $CF_3$, CN, $(C_1-C_4)$-alkyl, $(C_1-C_4)$-alkoxy, $(C_1-C_4)$-alkylthio or $(C_1-C_3)$-alkoxy) carbonyl, preferably in position 6 on the phenyl ring, n is 1, 2 or 3, preferably 1, $R^{15}$ is hydrogen, $(C_1-C_4)$-alkyl or $(C_3-C_4)$-alkenyl, $R^{13}$, $R^{17}$ independently of one another are halogen, $(C_1-C_2)$-alkyl, $(C_1-C_2)$-alkoxy, $(C_1-C_2)$-haloalkyl, $(C_1-C_2)$-haloalkoxy or $(C_1-C_2)$-alkoxy-$(C_1-C_2)$-alkyl, preferably $OCH_3$ or $CH_3$, for example 3-(4,6-dimethoxypyrimidin-2-yl)-1-(2-ethoxyphenoxy) sulfonylurea, or salts thereof;

B7) imidazolylsulfonylureas, for example MON 37500, sulfosulfuron (see Brighton Crop Prot. Conf. 'Weeds', 1995, p: 57), and other related sulfonylurea derivatives and mixtures thereof;

C) chloroacetanilides, for example N-methoxymethyl-2,6-diethylchloroacetanilide (alachlor), N-(3-methoxyprop-2-yl)-2-methyl-6ethylchloroacetanilide (metolachlor), 2,6-dimethyl-N-(3-methyl-1,2,4-oxadiazol-5-ylmethyl) chloroacetanilide, N-(2,6-dimethylphenyl)-N-(1-pyrazolylmethyl)chloroacetamide (metazachlor);

D) thiocarbamates, for example Sethyl-N,N-dipropylthiocarbamate (EPTC), S-ethyl-N,N-diisobutylthiocarbamate (butylate);

E) cyclohexanedione oximes, for example methyl 3-(1-allyloxyiminobutyl)4-hydroxy6,6-dimethyl-2-oxocyclohex-3-enecarboxylate (alloxydim), 2-(1-ethoxyiminobutyl)-5-(2-ethylthiopropyl)-3-hydroxycyclohex-2-en-1-one (sethoxydim), 2-(1-ethoxyiminobutyl)-5-(2-phenylthiopropyl)-3-hydroxycyclohex-2-en-1-one (cloproxydim), 2-(1-(3-chloroallyloxy)iminobutyl)-5-(2-ethylthiopropyl)-3-hydroxycyclohex-2-en-1-one, 2-(1-(3-chloroallyloxy)iminopropyl)-5-(2-ethylthiopropyl)-3-hydroxycyclohex-2-en-1-one (clethodim), 2-(1-ethoxyiminobutyl)-3-hydroxy-5-(thian-3-yl)-cyclohex-2-enone (cycloxydim), 2-(1-ethoxyiminopropyl)-5-(2,4,6-trimethylphenyl)-3-hydroxycyclohex-2-en-1-one (tralkoxydim);

F) imidazolinones, for example methyl 2-(4-isopropyl4-methyl-5-oxo-2-imidazolin-2-yl)-5-methylbenzoate and 2-(4-isopropyl-4-methyl-5oxo-2-imidazolin-2-yl)4-methylbenzoic acid (imazamethabenz), 5-ethyl-2-(4-isopropyl4-methyl-5-oxo-2-imidazolin-2-yl)pyridin-3-carboxylic acid (imazethapyr), 2-(4-isopropyl-4-methyl-5-oxo-2-imidazolin-2-yl)quinolin-3-carboxylic acid (imazaquin), 2-(4-isopropyl4-methyl-5-oxo-2-imidazolin-2-yl)-pyridin-3-carboxylic acid (imazapyr), 5-methyl-2-(4-isopropyl4-methyl-5-oxo-2-imidazolin-2-yl)pyridin-3-carboxylic acid (imazethamethapyr);

G) triazolopyrimidinsulfonamide derivatives, for example N-(2,6-difluorophenyl)-7-methyl-1,2,4-triazolo[1,5,c]pyrimidin-2-sulfonamide (flumetsulam), N-(2,6-dichloro-3-methylphenyl)-5,7-dimethoxy-1,2,4-triazolo[1,5-c]pyrimidin-2-sulfonamide, N-(2,6-difluorophenyl)-7-fluoro-5-methoxy-1,2,4-triazolo[1,5-c]pyrimidin-2-sulfonamide, N-(2,6-dichloro-3-methylphenyl)-7-chloro-5-methoxy-1,2,4-triazolo[1,5-c]pyrimidin-2-sulfonamide, N-(2 chloro-6-methoxycarbonyl)-5,7-dimethyl-1,2,4-triazolo[1,5-c]pyrimidin-2-sulfonamide (EP-A 0 343 752, US-A 4,988, 812);

H) benzoylcyclohexanediones, for example 2-(2-chloro4-methylsulfonylbenzoyl)cyclohexane-1,3-dione (SC-0051, EP-A 0 137 963), 2-(2-nitrobenzoyl)-4,4-dimethylcyclohexane-1,3-dione (EP-A 0 274 634), 2-(2-nitro-3-methylsulfonylbenzoyl)-4,4-dimethylcyclohexane-1,3-dione (WO 91/13548);

I) pyrimidinyloxypyridinecarboxylic acid or pyrimidinyloxybenzoic acid derivatives, for example benzyl 3-(4,6-dimethoxypyrimidin-2-yl)oxypyridin-2-carboxylate (EP-A 0 249 707), methyl 3-(4,6-dimethoxypyrimidin-2-yl) oxypyridin-2-carboxylate (EP-A 0 249 707), 2,6-bis[(4,6-dimethoxypyrimidin-2-yl)oxy]benzoic acid (EP-A 0 321 846), 1-(ethoxycarbonyloxyethyl) 2,6-bis[(4,6-dimethoxypyrimidin-2-yl)oxy]benzoate (EP-A 0 472 113);

J) S-(N-aryl-N-alkylcarbamoylmethyl)dithiophosphonic acid esters, such as S-[N-(4-chlorophenyl)-N-isopropylcarbamoylmethyl] O,O-dimethyl dithiophosphate (anilophos).

The herbicides of groups A to J are known, for example, from the above-mentioned publications and from "The Pesticide Manual", The British Crop Protection Council and the Royal Soc. of Chemistry, 10th Edition, 1994, "Agricultural Chemicals Book II—Herbicides—", by W. T. Thompson, Thompson Publications, Fresno Calif., U.S.A 1990 and "Farm Chemicals Handbook '90", Meister Publishing Company, Willoughby Ohio, U.S.A,1990.

The weight ratio of safener to pesticide can be varied within wide limits and is preferably in the range from 1:10 to 10:1, in particular 1:10 to 5:1. The optimum weight ratio of safener to pesticide depends both on the active compounds safener and pesticide employed and on the kind of useful plants to be protected. The required safener application rate can, depending on the pesticide employed and the kind of useful plant to be protected, be varied within wide limits and is usually in the range from 0.001 to 5 kg, preferably 0.005 to 0.5 kg, of safener per hectare. The amounts and weight ratios required for a successful treatment can be determined by simple preliminary tests.

In general, the compositions according to the invention can be employed for protecting various crops of useful plants such as cotton, cereals, maize, rapeseed, rice and soybean. Preferred crops of useful plants are cereals and maize.

The safeners of the formula I according to the invention have a particular advantage in combination with herbicides from the group of the sulfonylureas and/or imidazolinones and with herbicides of the type of the phenoxyphenoxy- and heteroaryloxyphenoxyalkanecarboxylic acid derivatives. This is because a large number of herbicides of these structural classes cause considerable damage to useful plants, in particular in crops of cereals, in maize and rice, and they can therefore not always be employed in these crops. By combination with the safeners according to the invention, excellent selectivities can be achieved in cereals, maize or rice, even when using these herbicides.

The compounds of the formula I and their combinations with one or more of the abovementioned pesticides can be formulated in various ways, depending on the prevailing chemical-physical and biological parameters.

Examples of suitable formulations are:

emulsifiable concentrates which are prepared by dissolving the active compounds in an organic solvent, for example butanol, cyclohexanone, dimethylformamide, xylene or else higher-boiling hydrocarbons or mixtures of the organic solvents with addition of one or more ionic and/or nonionic surfactants (emulsifiers). Suitable emulsifiers are, for example, calcium alkylarylsulfonates, fatty acid polyglycol esters, alkylaryl polyglycol ethers, fatty alcohol polyglycol ethers, propylene oxide/ethylene oxide condensates, alkyl polyethers, sorbitan esters and polyoxyethylenesorbitan fatty acid esters dusts, which are obtained by grinding the active compounds with finely dispersed solid inorganic or organic substances, for example talc, natural clays, such as kaolin, bentonite and pyrophyllite, diatomaceous earth or meals water- or oil-based suspension concentrates, which can be prepared, for example, by wet grinding using bead mills water-soluble powders water-soluble concentrates granules, such as water-soluble granules, water-dispersible granules and granules for application by broadcasting and soil application wettable powders, which, in addition to active compound, also contain diluents or inert substances and surfactants capsule suspensions and microcapsules ultra-low-volume formulations.

The abovementioned formulation types are known to the person skilled in the art and described, for example, in: K. Martens, "Spray Drying Handbook", 3rd Ed., G. Goodwin Ltd., London. 1979; W. van Valkenburg, "Pesticide Formulations", Marcel Dekker, N.Y. 1973; Winnaker-Küchler, "Chemische Technologie" [Chemical Technology], Volume 7, C. Hauser Verlag Munich, 4th Edition 1986; "Perry's Chemical Engineer's Handbook", 5th Ed., McGraw-Hill, N.Y. 1973, pages 8–57.

The formulation auxiliaries required, such as inert materials, surfactants, solvents and further additives are also known and are described, for example, in: McCutcheon's "Detergents and Emulsifiers Annual", MC Publ. Corp., Ridgewood N.J.; C. Marsden, "Solvents Guide", 2nd Ed., Interscience, N.Y. 1963; H. von Olphen, "Introduction to Clay Colloid Chemistry", 2nd Ed., J. Wiley & Sons, N.Y.; Schönfeldt, "Grenzflächenaktive Äthylenoxidaddukte" [Surface-Active Ethylene Oxide Adducts], Wiss. Verlagsgesellschaft, Stuttgart 1976; Sisley and Wood, "Encyclopedia of Surface Active Agents", Chem. Publ. Co. Inc., N.Y. 1964; Watkins, "Handbook of Insecticide Dust Diluents and Carriers", 2nd Ed., Darland Books, Caldwell N.J.; Winnacker-Küchler, "Chemische Technologie", Volume 7, C. Hauser Verlag Munich, 4th Edition 1986.

In addition to the abovementioned formulation auxiliaries, the crop protection compositions may comprise, if appropriate, customary tackifiers, wetting agents, dispersants, penetrants, emulsifiers, preservatives, antifreeze agents, fillers, carriers, colorants, anti-foams, evaporation inhibitors and pH and viscosity regulators.

Depending on the formulation type, the crop protection compositions generally comprise 0.1 to 99% by weight, in particular 0.2 to 95% by weight, of one or more safeners of the formula I or a combination of safener and pesticide. Furthermore, they comprise 1 to 99.9, in particular 4 to 99.5, % by weight of one or more solid or liquid additives and 0 to 25, in particular 0.1 to 25, % by weight of a surfactant. In emulsifiable concentrates, the active compound concentration, i.e. the concentration of safener and/or pesticide, is generally 1 to 90, in particular 5 to 80, % by weight. Dusts usually comprise 1 to 30, preferably 5 to 20, % by weight of active compound. In wettable powders, the active compound concentration is generally 10 to 90% by weight. In water-dispersible granules, the active compound content is, for example, between 1 and 95% by weight, preferably between 10 and 80% by weight.

For use, the formulations which are present in commercial form are, if appropriate, diluted in a customary manner, for example in the case of wettable powders, emulsifable concentrates, dispersions and water-dispersible granules with water. Dust preparations, granules and sprayable solutions are usually not diluted with any further inert substances prior to use. The required rate of application of the safeners varies with the external conditions such as, inter alia, temperature, humidity, and the kind of herbicide employed.

The compounds of the formula I can be prepared, for example, by a) reacting a compound of the formula II

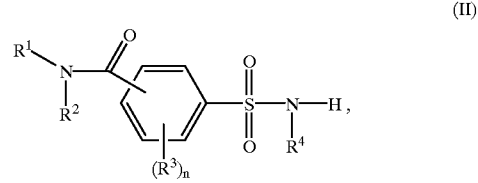

where $R^1$, $R^2$, $R^3$, $R^4$ and n are as defined above, with an acylating agent, for example a carbonyl halide, carboxylic anhydride or carbonylimidazolide, of the formula III

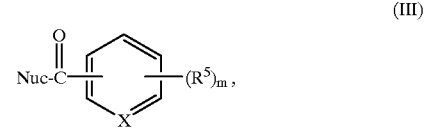

where Nuc is a leaving group and X, $R^5$ and m are as defined above, or reacting a compound of the formula III in which Nuc is hydroxyl with the sulfonamide of the formula II using coupling agents such as dicyclohexylcarbodiimide, or b) reacting a compound of the formula IV

where $R^1$ and $R^2$ are as defined above, with suitable activated carboxylic acid derivatives of the formula V

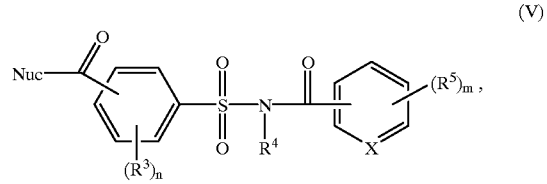

where X, $R^3$, $R^4$, $R^5$, n and m are as defined above and Nuc is a leaving group.

The reactions according to variants a) and b) are preferably carried out in an inert organic solvent in the presence of an acid binder. Suitable solvents are, for example, aprotic polar solvents, for example ethers, such as THF (tetrahydrofuran), dioxane, acetonitrile and dimethylformamide. Suitable acid binders are bases, preferably organic bases, such as triethylamine, pyridine, dimethylaminopyridine, DBU (1,8-diazabicyclo[5.4.0]-undec-7-ene), DBN (1,5-diazabicyclo[4.3.0]non-5-ene) and 1,4-diazabicyclo[2.2.2]octane. The reaction temperatures are preferably in the range between –20° C. and 120° C. The compounds of the formulae II, III, IV and V are either commercially available or can be prepared by methods known to the person skilled in the art.

EXAMPLES

1 Formulation Examples 1.1 Dustic Agents

A dusting agent is obtained by mixing 10 parts by weight of a compound of the formula I or of an active compound mixture of a herbicide and a safener of the formula I and 90 parts by weight of talc as inert material and comminuting in a hammer mill.

1.2 Water-dispersible Powder

A wettable powder which is readily dispersible in water is obtained by mixing 25 parts by weight of a compound of the formula I or of an active compound mixture of a herbicide and a safener of the formula I, 64 parts by weight of kaolin-containing quartz as inert material, 10 parts by weight of potassium ligninsulfonate and 1 part by weight of sodium oleoylmethyltaurinate as wetting and dispersing agent, and grinding in a pin mill.

1.3 Water-dispersible Concentrate

A dispersion concentrate which is readily dispersible in water is obtained by mixing 20 parts by weight of a compound of the formula I or of an active compound mixture of a herbicide and a safener of the formula I with 6 parts by weight of alkylphenol polyglycol ether (®Triton X 207), 3 parts by weight of isotridecanol polyglycol ether and 71 parts by weight of paraffinic mineral oil and grinding in a ball mill to a fineness of below 5 microns.

1.4 Emulsifiable Concentrate

An emulsifiable concentrate is obtained from 15 parts by weight of a compound of the formula I or of an active compound mixture of a herbicide and a safener of the formula I, 75 parts by weight of cyclohexanone as solvent and 10 parts by weight of ethoxylated nonylphenol as emulsifier.

1.5 Water-dispersible Granules

Water dispersible granules are obtained by mixing

| | | |
|---|---|---|
| 75 parts by weight | of a safener of the formula I or of a mixture of a pesticide and a safener of the formula I, |
| 10 parts by weight | of calcium ligninsulfonate, |
| 5 parts by weight | of sodium lauryl sulfate, |
| 3 parts by weight | of polyvinyl alcohol and |
| 7 parts by weight | of kaolin, | grinding in a pin mill and granulating the powder in a fluidized bed by spraying on water as granulation liquid.

Water-dispersible granules are also obtained by homogenizing

| | | |
|---|---|---|
| 25 parts by weight | of a safener of the formula I or of a mixture of a pesticide and a safener of the formula I, |
| 5 parts by weight | of sodium 2,2'-dinaphthylmethane-6,6'-disulfonate, |
| 2 parts by weight | of sodium oleoylmethyltaurinate, |
| 17 parts by weight | of calcium carbonate, |
| 50 parts by weight | of water and |
| 1 part by weight | of polyvinyl alcohol | in a colloid mill, comminuting, then grinding in a bead mill and atomizing and drying the resulting suspension in a spray tower using a single-fluid nozzle.

2 Preparation Examples

2.1 4-(2-Chlorobenzoylsulfamoyl)-N-propylbenzamide

Examples 1–19 of Table 1

2.1.1 N-propyl4-sulfamoylbenzamide

At room temperature, 10 g (0.05 mol) of 4-sulfamoylbenzoic acid are dissolved in 100 ml of tetrahydrofuran and admixed with 8.1 g (0.05 mol) of N,N'-carbonyldiimidazole. After 30 minutes at room temperature and a further 30 minutes at reflux temperature, 2.9 g (0.05 mol) of propylamine are added at room temperature. After 2 hours, the reaction mixture is concentrated and stirred with water, the precipitate is filtered off with suction and dried.

Yield: 8.8 g (70%); mp.: 203° C.

2.1.2 4-(2-Chlorobenzoylsufamoyl)-N-propylbenzamide

At room temperature, 1.3 g (8.3 mmol) of 2-chlorobenzoic acid are dissolved in 100 ml of tetrahydrofuran and admixed with 1.3 g (8.3 mmol) of N,N'-carbonyidiimidazole. After 30 minutes at room temperature and a further 30 minutes at reflux temperature, 2.0 g (8.3 mmol) of N-propyl-4-sulfamoylbenzamide are added at reflux temperature. After 10 minutes, 1.2 g (8.3 mmol) of 1,5-diazabicyclo[5.4.0]- 5-undecene are added and the mixture is kept at reflux temperature for a further 3 hours. The mixture is then concentrated to dryness, the residue is taken up in 60 ml of acetonitrile and the solution is poured into 60 ml of water. The solution is acidified to pH 1 using 2N HCl and the precipitate is separated off, washed with water and dried.

Yield: 1.8 g (54%); mp.: 210° C.

2.2 2,4-Dichloro-5-(2-Chlorobenzoylsulfamoyl)-N-(2-Methoxyethyl)Benzamide

Examples 2–39 of Table 2

2.2.1. 2,4-Dichloro-N-2-Methoxyethyl)-5-Sulfamoylbenzamide 15 g (56 mmol) of 2,4-dichloro-5-sulfamoylbenzoic acid are dissolved in 350 ml of tetrahydrofuran and, at room temperature, admixed with 9 g (56 mmol)of N,N'-carbonyidiimidazole. After 30 minutes at room temperature and a further 30 minutes at reflux temperature, 4.2 g (56 mmol) of 2-methoxyethylamine are added at room temperature. After 4 hours, the reaction mixture is concentrated and stirred with water and the precipitate is filtered off with suction and dried.

Yield: 11.7 g (61%); mp.: 158° C.

2.2.2. 2,4-Dichloro-5-(2-Chlorobenzoylsulfamoyl)-N-(2-Methoxyethyl)Benzamide At room temperature, 1.0 g (6.1 mmol) of 2-chlorobenzoic acid are dissolved in 120 ml of tetrahydrofuran and mixed with 1.0 g (6.1 mmol) of N,N'-carbonyldiimidazole. After 30 minutes at room temperature and a further 30 minutes at reflux temperature, 2.0 g (6.1 mmol) of 2,4-dichloro-N-(2-methoxyethyl)-5-sulfamoylbenzamide are added at reflux temperature. After 10 minutes, 0.9 g (6.1 mmol) of 1,5-diazabicyclo[5.4.0]-5-undecene are added and the mixture is kept at reflux temperature for a further 3 hours. The mixture is subsequently evaporated to dryness, the residue is taken up in 60 ml of acetonitrile and the solution is poured into 60 ml of water. The solution is acidified to pH 1 using 2N HCl and the precipitate is separated off, washed with water and dried.

Yield: 1.8 g (61%); mp.: 181° C.

3 Biological Examples

3.1 Scoring of the Damage

The damage to the plants is assessed visually on a scale of 0–100% in comparison with control plants:

0%=no noticeable effect in comparison with the untreated plant
100%=the treated plant dies off.

3.2 Effect of the Herbicide and Effect of the Safener when Applied Pre-emergence Seeds or rhizome pieces of mono- and dicotyledonous harmful plants and of crop plants are placed in sandy loam soil in plastic pots of a diameter of 9 cm and covered with soil. Alternatively, harmful plants encountered in paddy rice cultivation are cultivated in water-saturated soil, where the amount of water poured into the pots is such that the water level is at the soil surface, or some millimeters above the soil surface. The herbicidelsafener active compound combinations according to the invention, formulated in the form of emulsion concentrates, and, in parallel tests, the correspondingly formulated individual active compounds are then applied as emulsions to the surface of the soil cover in various dosages using an amount of water of 300 I/ha (converted), or, in the case of rice, are poured into the irrigation water. After the treatment, the pots are placed in a greenhouse and kept under good growth conditions for the weeds. Visual scoring of the damage to the plants or the emerging plants was carried out in comparison with untreated controls after the test plants had emerged after a test period of 2–3 weeks. The tests show that the herbicidal compositions according to the invention which comprise, for example, a safener of Examples 1–17, 1–20, 1–33, 1–67, 1–68, 1–69, 1–70, 1–75, 1–76, 1–84, 1–85, 1–86, 1–117, 1–118, 1–133, 1–150, 1–151, 1–153, 1–162, 1–163, 1–195, 1–197 in combination with the sulfonylurea herbicide 3-(4,6-dimethoxypyrimid-2-yl)-1-[3-(N-methylsulfonyl-N-methylamino)pyridyl-2-ylsulfonyl]urea or 3-(4-methoxy-6-methyl-1,3,5-triazin-2-yl)-1-(2-methoxycarbonyl-5-iodophenylsulfonyl)urea (sodium salt) or 1-(2-methoxycarbonylthiophen-3-yl)-3-(4-methoxy-6-methyl-1,3,5-triazin-2-yl)urea (thifensulfuron-methyl) or 1-(3-N,N-dimethylaminocarbonylpyridin-2-ylsulfonyl)-3-(4,6-dimethoxypyrimidin-2-yl)urea (nicosulfuron) or 1-(3-ethylsulfonylpyridin-2-ylsulfonyl)-3-(4,6-dimethoxypyrimidin-2-yl)urea (rimsulfuron) or N,N-dimethyl-2-[3-(4,6-dimethoxypyrimidin-2-yl)ureidosulfonyl]-4-formylaminobenzamide or methyl 2-[3-(4,6-dimethoxypyrimidin-2-yl)-ureidosulfonyl]4-methanesulfonamidomethylbenzoate or with the imidazolinone herbicide 5-ethyl-2-(4-isopropyl4-methyl-5-oxo-2-imidazolin-2-yl)pyridin-3-carboxylic acid (imazethapyr) or with the aryloxyphenoxy herbicide ethyl 2-(4-(6-chloro-benzoxazol-2-yloxy)phenoxy)propionate (fenoxaprop-ethyl) or with 2,6-bis[(4,6-dimethoxypyrimidin-2-yl)-oxy]benzoic acid sodium salt in a ratio of herbicide:safener of 2:1 to 1:20 have good herbicidal pre-emergence activity against a broad spectrum of broad-leaved weeds and weed grasses, and damage to crop plants such as maize, rice, wheat or barley or other cereals is considerably reduced in comparison with application of individual herbicides without safener, i.e. they show from about 30% to up to 100% less damage by herbicides.

3.3 Effect of the Herbicide and Effect of the Safener when Applied Post-Emergence Seeds or rhizome pieces of mono- and dicotyledenous harmful plants and of crop plants are placed in sandy loam soil in plastic pots, covered with soil and cultivated in a greenhouse under good growth conditions. Alternatively, harmful plants encountered in paddy rice cultivation are cultivated in pots where the water level is up to 2 cm above the soil surface. Three weeks after sowing, the test plants are treated at the three-leaf stage. The herbicide/safener active compound combinations according to the invention, formulated as emulsion concentrates, and, in parallel tests, the correspondingly formulated individual active compounds are sprayed onto the green parts of the plants in various dosages using an amount of water of 300 I/ha (converted) and, after the test plants have been kept in the greenhouse for 2–3 weeks under optimum growth conditions, the effect of the preparations is scored visually in comparison to untreated controls. In the case of rice or of harmful plants encountered in rice cultivation, the active compounds are also added directly to the irrigation water (application similar to granules application) or sprayed onto plants and into the irrigation water. The tests show that the herbicidal compositions according to the invention which comprise, for example, a safener of Examples 1–17, 1–20, 1–33, 1–67, 1–68, 1–69, 1–70, 1–75, 1–76, 1–84, 1–85, 1–86, 1–117, 1–118, 1–133, 1–150, 1–151, 1–153, 1–162, 1–163, 1–195, 1–197 in combination with the sulfonylurea herbicide 3-(4,6-dimethoxypyrimidin-2-yl)-1-[3-(N-methylsulfonyl-N-methylamino)pyridyl-2-ylsulfonyl]urea or 3-(4-methoxy-6-methyl-I,3,5-triazin-2-yl)-1-(2-methoxycarbonyl-5-iodophenylsulfonyl)urea (sodium salt) or 1-(2-methoxycarbonylthiophen-3-yl)-3-(4-methoxy-6-methyl-1,3,5-triazin-2-yl)urea (thifensulfuron-methyl) or 1-(3-N,N-dimethylaminocarbonylpyridin-2-ylsulfonyl)-3-(4,6-dimethoxypyrimidin-2-yl)urea (nicosulfuron) or 1-(3-ethylsulfonylpyridin-2-ylsulfonyl)-3-(4,6-dimethoxypyrimidin-2-yl)urea (rimsulfuron) or N,N-dimethyl-2-[3-(4,6-dimethoxypyrimidin-2-yl)ureidosulfonyl]-4-formylaminobenzamide or methyl 2-[3-(4,6-dimethoxypyrimidin-2-yl)-ureidosulfonyl]-4-methanesulfonamidomethylbenzoate or with the imidazolinone herbicide 5-ethyl-2-(4-isopropyl-4-methyl-5-oxo-2-imidazolin-2-yl)pyridin-3-carboxylic acid (imazethapyr) or with the aryloxyphenoxy herbicide ethyl 2-(4-(6-chlorobenzoxazol-2-yloxy)phenoxy)propionate (fenoxaprop-ethyl) or with 2,6-bis[(4,6-dimethoxy-pyrimidin-2-yl)-oxy]benzoic acid sodium salt in a ratio of herbicide:safener of 2:1 to 1:20 have good herbicidal post-emergence activity against a broad spectrum of broad-leaved weeds and weed grasses, and damage to crop plants such as maize, rice, wheat or barley or other cereals is considerably reduced in comparison with application of individual herbicides without safener, i.e. they show from about 30% to up to 100% less damage by herbicides.

In the tables below, a number of compounds of the formula I which can be obtained in a manner similar to the abovementioned examples and the methods mentioned further above are listed by way of example.

The abbreviations in the tables denote:

| Bu | = butyl | Et | = ethyl |
|---|---|---|---|
| Me | = methyl | Nap | = naphthoyl |
| Pr | = propyl | c | = cyclo |
| i | = iso | s | = secondary |
| t | = tertiary | m.p. | = melting point |

If an alkyl radical is listed in the tables without any further specification, this alkyl radical is straight-chain.

TABLE 1

[Structure: R¹R²N-C(=O)-[benzene ring positions 1,2,3,4,5,6 with (R³)ₙ]-S(=O)₂-N(R⁴)-C(=O)-[benzene ring with (R⁵)ₘ]]

| No. | R¹ | R² | R³ | R⁴ | R⁵ | m.p. [° C.] |
|---|---|---|---|---|---|---|
| 1-1 | Bu | H | — | H | 2-OMe | 178 |
| 1-2 | Bu | H | — | H | 2-OMe, 5-Me | 196 |
| 1-3 | Bu | H | — | H | 2-Cl | 131 |
| 1-4 | Bu | H | — | H | 2-OMe, 5-Cl | 209 |
| 1-5 | Bu | H | — | H | 2-NO₂, 4-Cl | |
| 1-6 | Bu | H | — | H | 2,5-(Me)₂ | |
| 1-7 | Bu | H | — | H | 2,3-(Me)₂ | |
| 1-8 | Bu | H | — | H | 2-NO₂, 4-Cl | |
| 1-9 | Bu | H | — | Me | 2-OMe | |
| 1-10 | Bu | H | — | Me | 2-OMe, 5-Me | |
| 1-11 | Bu | H | — | Me | 2-Cl | |
| 1-12 | Bu | H | — | Me | 2-OMe, 5-Cl | |
| 1-13 | Bu | H | 2-NO₂ | H | 2-OMe | |
| 1-14 | Bu | H | 2-NO₂ | H | 2-OMe, 5-Me | |
| 1-15 | Bu | H | 2-NO₂ | H | 2-Cl | |
| 1-16 | Bu | H | 2-NO₂ | H | 2-OMe, 5-Cl | |
| 1-17 | Pr | H | — | H | 2-OMe | 170 |
| 1-18 | Pr | H | — | H | 2-Me | 120 |
| 1-19 | Pr | H | — | H | 2-Cl | 210 |
| 1-20 | Pr | H | — | H | 2-OMe, 5-Me | 170 |
| 1-21 | Pr | H | — | H | 2-OMe, 5-Cl | 180 |
| 1-22 | Pr | H | — | H | 2,3-(Me)₂ | 200 |
| 1-23 | Pr | H | — | H | 2-NO₂, 4-Cl | |
| 1-24 | Pr | H | 2-NO₂ | H | 2-OMe, 5-Cl | |
| 1-25 | Pr | H | 2-NO₂ | H | 2,3-(Me)₂ | |
| 1-26 | Pr | H | 2-NO₂ | H | 2-OMe, 5-Me | |
| 1-27 | Pr | H | 2-NO₂ | H | 2-OMe | 197 |
| 1-28 | Pr | H | — | Me | 2-OMe, 5-Cl | |
| 1-29 | Pr | H | — | Me | 2,3-(Me)₂ | |
| 1-30 | Pr | H | — | Me | 2-OMe, 5-Me | |
| 1-31 | Pr | H | — | Me | 2-OMe | |
| 1-32 | Pr | H | 2-NO₂ | Me | 2-OMe, 5-Me | |
| 1-33 | allyl | H | — | H | 2-OMe, 5-Me | 161 |
| 1-34 | allyl | H | — | H | 2-Me | 195 |
| 1-35 | allyl | H | — | H | 2,5-Cl₂ | 178 |
| 1-36 | allyl | H | — | H | 2,3-(Me)₂ | 185 |
| 1-37 | allyl | H | — | H | 2,5-(Me)₂ | 181 |
| 1-38 | allyl | H | — | H | 2-OMe, 5-Cl | 174 |
| 1-39 | allyl | H | — | H | 2-Cl | 201 |
| 1-40 | allyl | H | 2-NO₂ | H | 2-OMe, 5-Cl | |
| 1-41 | allyl | H | 2-NO₂ | H | 2-OMe | |
| 1-42 | allyl | H | — | Me | 2,5-(Me)₂ | |
| 1-43 | allyl | H | — | Me | 2-OMe, 5-Me | |
| 1-44 | allyl | H | — | H | 2-NO₂, 4-Cl | |
| 1-45 | allyl | Allyl | — | H | 2,5-Cl₂ | 125 |
| 1-46 | allyl | Allyl | — | H | 2-Me | 120 |
| 1-47 | allyl | Allyl | — | H | 2-OMe, 5-Me | 120 |
| 1-48 | allyl | Allyl | — | H | 2-OMe, 5-Cl | 105 |
| 1-49 | allyl | Allyl | — | H | 2,3-(Me)₂ | 158 |
| 1-50 | allyl | Allyl | — | H | 2-Cl | 96 |
| 1-51 | allyl | Allyl | — | H | 2,5-(Me)₂ | 144 |
| 1-52 | allyl | H | — | H | 1-MeO-2-Nap | 180 |
| 1-53 | allyl | Me | — | H | 2-Me | 171 |
| 1-54 | allyl | Me | — | H | 2-OMe | |
| 1-55 | allyl | Me | — | H | 2-OMe, 5-Me | |
| 1-56 | allyl | Me | — | H | 2-OMe, 5-Cl | 214 |
| 1-57 | allyl | Me | — | H | 2,3-(Me)₂ | |
| 1-58 | c-hexyl | H | — | H | 2-Cl | |
| 1-59 | c-hexyl | H | 2-NO₂ | H | 2-OMe, 5-Me | |
| 1-60 | c-hexyl | H | — | Me | 2-OMe, 5-Cl | |
| 1-61 | c-pentyl | H | — | H | 2-OMe | 206 |
| 1-62 | c-pentyl | H | — | H | 2-Me | 188 |
| 1-63 | c-pentyl | H | — | H | 2-Cl | 220 |
| 1-64 | c-pentyl | H | — | H | 2-OMe, 5-Me | |
| 1-65 | c-pentyl | H | 2-NO₂ | H | 2-OMe, 5-Me | |
| 1-66 | c-pentyl | H | — | Me | 2-OMe, 5-Me | |
| 1-67 | c-Pr | H | — | H | 2-OMe | 218 |
| 1-68 | c-Pr | H | — | H | 2-Cl | 207 |

TABLE 1-continued

[Structure: R¹R²N-C(=O)-[benzene ring with positions 1,2,3,4,5,6 and (R³)ₙ at position 3]-S(=O)₂-N(R⁴)-C(=O)-[benzene ring with (R⁵)ₘ]]

| No. | R¹ | R² | R³ | R⁴ | R⁵ | m.p. [° C.] |
|---|---|---|---|---|---|---|
| 1-69 | c-Pr | H | — | H | 2-Me | 226 |
| 1-70 | c-Pr | H | — | H | 2-OMe, 5-Me | 211 |
| 1-71 | c-Pr | H | — | H | 2,5-Cl₂ | 229 |
| 1-72 | c-Pr | H | — | H | 2-NO₂, 4-Cl | 205 |
| 1-73 | c-Pr | H | — | H | 2-OMe, 5-Cl | 208 |
| 1-74 | c-Pr | H | — | H | 2,3-(Me)₂ | 233 |
| 1-75 | c-Pr | H | — | H | 2,5-(Me)₂ | 225 |
| 1-76 | c-Pr | H | — | Me | 2-OMe | 70 |
| 1-77 | c-Pr | H | — | Me | 2-Me | 122 |
| 1-78 | c-Pr | H | — | Me | 2,5-(Me)₂ | |
| 1-79 | c-Pr | H | — | Me | 2-OMe, 5-Me | |
| 1-80 | c-Pr | H | 2-NO₂ | H | 2,5-(Me)₂ | |
| 1-81 | c-Pr | H | 2-NO₂ | H | 2-OMe, 5-Me | |
| 1-82 | C₂H₄—OEt | H | — | H | 2-Cl | 138 |
| 1-83 | C₂H₄—OEt | H | — | H | 2-OMe | 161 |
| 1-84 | C₂H₄—OEt | H | — | H | 2-Me | 162 |
| 1-85 | C₂H₄—OEt | H | — | H | 2-OMe | 187 |
| 1-86 | C₂H₄—OEt | H | — | H | 2-Cl | 163 |
| 1-87 | C₂H₄—OEt | H | — | H | 2,5-(Me)₂ | 179 |
| 1-88 | C₂H₄—OEt | H | — | H | 2,5-Cl₂ | 185 |
| 1-89 | C₂H₄—OEt | H | — | H | 2,3-(Me)₂ | 195 |
| 1-90 | C₂H₄—OEt | H | — | H | 2-Me | 159 |
| 1-91 | C₂H₄—OEt | H | — | H | 2-OMe, 5-Me | 186 |
| 1-92 | C₂H₄—OEt | H | — | H | 2-NO₂, 4-Cl | |
| 1-93 | C₂H₄—OEt | H | — | H | 2-OMe, 5-Cl | 193 |
| 1-94 | C₂H₄—OEt | H | — | Me | 2,3-(Me)₂ | |
| 1-95 | C₂H₄—OEt | H | — | Me | 2-Me | |
| 1-96 | C₂H₄—OEt | H | — | Me | 2-OMe, 5-Me | |
| 1-97 | C₂H₄—OEt | H | — | Me | 2-OMe, 5-Cl | |
| 1-98 | C₃H₆—OMe | H | — | H | 2-OMe | 142 |
| 1-99 | C₃H₆—OMe | H | — | H | 2-Me | 93 |
| 1-100 | C₃H₆—OMe | H | — | H | 2-Cl | 147 |
| 1-101 | CH₂-2-furanyl | H | — | H | 2-Me | 205 |
| 1-102 | CH₂-2-furanyl | H | — | H | 2-OMe | 190 |
| 1-103 | CH₂-2-furanyl | H | — | H | 2-Cl | 207 |
| 1-104 | CH₂-2-furanyl | H | — | H | 2,3-(Me)₂ | 170 |
| 1-105 | CH₂-2-furanyl | H | — | H | 2,5-Cl₂ | 200 |
| 1-106 | CH₂-2-furanyl | H | — | H | 2,5-(Me)₂ | 163 |
| 1-107 | CH₂-c-Pr | H | — | H | 2,5-Cl₂ | 209 |
| 1-108 | CH₂-c-Pr | H | — | H | 2,5-(Me)₂ | 145 |
| 1-109 | CH₂-c-Pr | H | — | H | 2-Me | 115 |
| 1-110 | CH₂-c-Pr | H | — | H | 2-OMe, 5-Me | 182 |
| 1-111 | CH₂-c-Pr | H | — | H | 2-OMe, 5-Cl | 192 |
| 1-112 | CH₂-c-Pr | H | — | H | 2-Cl | 141 |
| 1-113 | CH₂-c-Pr | H | — | H | 2,3-(Me)₂ | 153 |
| 1-114 | CH₂C≡CH | H | — | H | 2,5-Cl₂ | 175 |
| 1-115 | CH₂C≡CH | H | — | H | 2,3-(Me)₂ | 192 |
| 1-116 | CH₂C≡CH | H | — | H | 2-Me | 215 |
| 1-117 | CH₂C≡CH | H | — | H | 2-OMe, 5-Me | 166 |
| 1-118 | CH₂C≡CH | H | — | H | 2,5-(Me)₂ | 185 |
| 1-119 | CH₂C≡CH | H | — | H | 2-OMe, 5-Cl | 182 |
| 1-120 | CH₂C≡CH | H | — | H | 2-NO₂, 4-Cl | |
| 1-121 | CH₂C≡CH | H | — | H | 2-Cl | 220 |
| 1-122 | CH₂C≡CH | H | 2-NO₂ | H | 2,5-(Me)₂ | |
| 1-123 | CH₂C≡CH | H | — | Me | 2,5-(Me)₂ | |
| 1-124 | CH₂C≡CH | CH₂C≡CH | — | H | 2,5-(Me)₂ | |
| 1-125 | CH₂C≡CH | CH₂C≡CH | — | H | 2-OMe, 5-Me | |
| 1-126 | CH₂C≡CH | CH₂C≡CH | — | Me | 2,5-(Me)₂ | |
| 1-127 | CH₂C≡CH | CH₂C≡CH | — | Me | 2-OMe, 5-Me | |
| 1-128 | CH₂-t-Bu | H | — | H | 2-Cl | 213 |
| 1-129 | CH₂-t-Bu | H | — | H | 2-OMe | 170 |
| 1-130 | CH₂-t-Bu | H | — | H | 2-Me | 176 |
| 1-131 | CH₂CH(OMe)₂ | H | — | H | 2-OMe | 130 |
| 1-132 | CH₂CH(OMe)₂ | H | — | H | 2-Me | 140 |
| 1-133 | Et | Et | — | H | 2-OMe | 136 |
| 1-134 | Et | Et | — | H | 2-Cl | 180 |
| 1-135 | Et | Et | — | H | 2,5-Cl₂ | 155 |
| 1-136 | Et | Et | — | H | 2-OMe | |

TABLE 1-continued

| No. | R¹ | R² | R³ | R⁴ | R⁵ | m.p. [° C.] |
|---|---|---|---|---|---|---|
| 1-137 | Et | H | — | H | 2,5-(Me)$_2$ | |
| 1-138 | Et | H | — | H | 2-OMe, 5-Me | |
| 1-139 | Et | H | — | H | 2-NO$_2$, 4-Cl | |
| 1-140 | Et | H | — | H | 2,3-(Me)$_2$ | |
| 1-141 | Et | H | — | Me | 2-OMe | |
| 1-142 | Et | H | — | Me | 2-OMe, 5-Me | |
| 1-143 | Et | H | 2-NO$_2$ | H | 2-OMe, 5-Me | |
| 1-144 | i-Bu | H | — | H | 2-OMe | 160 |
| 1-145 | i-Bu | H | — | H | 2-Me | 150 |
| 1-146 | i-Bu | H | — | H | 2-Cl | 169 |
| 1-147 | i-Bu | H | — | H | 2,3-(Me)$_2$ | |
| 1-148 | i-Bu | H | — | H | 2-OMe, 5-Me | |
| 1-149 | i-Bu | H | — | H | 2,5-(Me)$_2$ | |
| 1-150 | i-Pr | H | — | H | 2-Me | 200 |
| 1-151 | i-Pr | H | — | H | 2-OMe | 224 |
| 1-152 | i-Pr | H | — | H | 2-Cl | 228 |
| 1-153 | i-Pr | H | — | H | 2,4-Cl$_2$ | 258 |
| 1-154 | i-Pr | H | — | H | 2,5-Cl$_2$ | 243 |
| 1-155 | i-Pr | H | — | Me | 2-OMe, 5-Me | |
| 1-156 | i-Pr | H | — | Me | 2,5-(Me)$_2$ | |
| 1-157 | i-Pr | H | — | H | 2-NO$_2$, 4-Cl | |
| 1-158 | i-Pr | H | 2-NO$_2$ | H | 2-Me | |
| 1-159 | i-Pr | H | 2-NO$_2$ | H | 2-OMe, 5-Me | |
| 1-160 | i-Pr | H | 2-NO$_2$ | H | 2,5-(Me)$_2$ | |
| 1-161 | Me | H | — | H | 2,3-(Me)$_2$ | 227 |
| 1-162 | Me | H | — | H | 2,5-Cl$_2$ | 278 |
| 1-163 | Me | H | — | H | 2-Me | 205 |
| 1-164 | Me | H | — | H | 2-OMe, 5-Me | 201 |
| 1-165 | Me | H | — | H | 2,5-(Me)$_2$ | 231 |
| 1-166 | Me | H | — | H | 2-NO$_2$, 4-Cl | |
| 1-167 | Me | H | — | H | 2-Cl | 238 |
| 1-168 | Me | H | 2-NO$_2$ | H | 2-OMe, 5-Me | |
| 1-169 | Me | H | 2-NO$_2$ | H | 2,5-(Me)$_2$ | |
| 1-170 | Me | H | — | Me | 2-OMe, 5-Me | |
| 1-171 | Me | H | — | Me | 2,5-(Me)$_2$ | |
| 1-172 | Me | Et | — | H | 2-Cl | 188 |
| 1-173 | Me | Et | — | H | 2-OMe | 155 |
| 1-174 | Me | Et | — | H | 2-Me | 203 |
| 1-175 | Me | Et | — | H | 2-NO$_2$, 4-Cl | |
| 1-176 | Me | Et | — | H | 2-OMe, 5-Me | |
| 1-177 | Me | Et | 2-NO$_2$ | H | 2-OMe, 5-Me | |
| 1-178 | Me | Et | — | Me | 2,5-(Me)$_2$ | |
| 1-179 | Me | Me | — | H | 2-OMe | 136 |
| 1-180 | Me | Me | — | H | 2-Me | 246 |
| 1-181 | Me | Me | — | H | 2-Cl | 231 |
| 1-182 | Me | Me | — | H | 2-OMe, 5-Me | 150 |
| 1-183 | Me | Me | — | H | 2,5-(Me)$_2$ | 167 |
| 1-184 | Me | Me | — | H | 2,3-(Me)$_2$ | 205 |
| 1-185 | Me | Allyl | — | H | 2-Cl | 177 |
| 1-186 | —(CH$_2$)$_2$—O—(CH$_2$)$_2$— | | — | H | 2-OMe | 212 |
| 1-187 | —(CH$_2$)$_2$—O—(CH$_2$)$_2$— | | — | H | 2-Me | 231 |
| 1-188 | —(CH$_2$)$_2$—O—(CH$_2$)$_2$— | | — | H | 2-NO$_2$, 4-Cl | |
| 1-189 | —(CH$_2$)$_2$—O—(CH$_2$)$_2$— | | — | H | 2,5-(Me)$_2$ | |
| 1-190 | —(CH$_2$)$_2$—O—(CH$_2$)$_2$— | | — | H | 2-OMe, 5-Me | 230 |
| 1-191 | —(CH$_2$)$_2$—O—(CH$_2$)$_2$— | | — | H | 2-Cl | |
| 1-192 | —(CH$_2$)$_4$— | | — | H | 2,5-(Me)$_2$ | 212 |
| 1-193 | —(CH$_2$)$_4$— | | — | H | 2,5-Cl$_2$ | 201 |
| 1-194 | —(CH$_2$)$_4$— | | — | H | 2,3-(Me)$_2$ | 202 |
| 1-195 | —(CH$_2$)$_4$— | | — | H | 2-Me | 206 |
| 1-196 | —(CH$_2$)$_4$— | | — | H | 2-Cl | 225 |
| 1-197 | —(CH$_2$)$_4$— | | — | H | 2-OMe, 5-Me | |
| 1-198 | —(CH$_2$)$_4$— | | — | H | 2-OMe, 5-Cl | 73 |
| 1-199 | —(CH$_2$)$_4$— | | — | H | 1-MeO-2-Nap | 158 |
| 1-200 | —(CH$_2$)$_4$— | | — | H | 2-NO2, 4-Cl | |
| 1-201 | —(CH$_2$)$_5$— | | — | H | 2,5-(Me)$_2$ | 157 |
| 1-202 | —(CH$_2$)$_5$— | | — | H | 2,5-Cl$_2$ | |
| 1-203 | —(CH$_2$)$_5$— | | — | H | 2,3-(Me)$_2$ | |
| 1-204 | —(CH$_2$)$_5$— | | — | H | 2-Me | 195 |

TABLE 1-continued

| No. | R¹ | R² | R³ | R⁴ | R⁵ | m.p. [° C.] |
|---|---|---|---|---|---|---|
| 1-205 | —(CH₂)₅— | | — | H | 2-Cl | |
| 1-206 | —(CH₂)₅— | | — | H | 2-OMe, 5-Me | |
| 1-207 | —(CH₂)₅— | | — | H | 2-OMe, 5-Cl | 169 |
| 1-208 | —(CH₂)₅— | | — | H | 2-NO₂, 4-Cl | |
| 1-209 | —C₂H₄—C₆H₅ | H | — | H | 2-OMe, 5-Me | 158 |
| 1-210 | —C₂H₄—C₆H₅ | H | — | H | 2-OMe, 5-Cl | 172 |
| 1-211 | —C₂H₄—C₆H₅ | H | — | H | 2-NO₂, 4-Cl | |
| 1-212 | —C₂H₄—C₆H₅ | H | — | H | 2-OMe | 201 |
| 1-213 | —(CH₂)₄— | | — | Me | 2-OMe, 5-Cl | resin |
| 1-214 | Me | Et | — | Me | 2-OMe | 111 |
| 1-215 | Pr | Pr | — | H | 2-OMe, 5-Cl | 143 |
| 1-216 | Pr | Pr | — | H | 2,5-(Me)₂ | 134 |
| 1-217 | Et | H | — | H | 2-OMe | 285 |
| 1-218 | Et | H | — | H | 2-OMe, 5-Cl | 271 |
| 1-219 | CH₂C≡CH | CH₂C≡CH | — | H | 2-OMe, 5-Cl | 183 |
| 1-220 | CH(CH₃)—C₃H₇ | H | — | H | 2-OMe, 5-Cl | 177 |
| 1-221 | CH(CH₃)—C₃H₇ | H | — | H | 2-NO₂, 4-Cl | 206 |
| 1-222 | C₆H₅ | H | — | H | 2-OMe | 222 |
| 1-223 | C₆H₅ | H | — | H | 2-OMe, 5-Cl | 235 |
| 1-224 | 2,4-F₂—C₆H₃ | H | — | H | 2-OMe, 5-Cl | 264 |
| 1-225 | c-Pr | H | — | H | 2-O—CH₂CH₂-3 | 264 |
| 1-226 | s-Bu | H | — | H | 2-OMe, 5-Cl | 192 |
| 1-227 | s-Bu | H | — | H | 2-OMe | 183 |
| 1-228 | 2-heptyl | H | — | H | 2-OMe, 5-Cl | 110 |
| 1-229 | 2-heptyl | H | — | H | 2-OMe | 143 |
| 1-230 | Me | Me | — | H | 2-OMe, 5-Cl | 154 |
| 1-231 | Me | Et | — | Me | 2-Me | resin |
| 1-232 | c-Pr | H | 2-NO₂ | H | 2-OMe | 234 |
| 1-233 | Pr | H | 2-Cl | H | 2-Me | 76 |
| 1-234 | c-Pr | H | 2-Cl | H | 2-OMe | 244 |
| 1-235 | c-Pr | H | 2-Cl | H | 2-OMe-5-Cl | 199 |

TABLE 2

| No. | R¹ | R² | R³ | R⁴ | R⁵ | m.p [° C.] |
|---|---|---|---|---|---|---|
| 2-1 | Pr | H | 2,4-Cl₂ | H | 2,5-(Me)₂ | 159 |
| 2-2 | Pr | H | 2,4-Cl₂ | H | 2-OMe | 141 |
| 2-3 | Pr | H | 2,4-Cl₂ | H | 2-Cl | 127 |
| 2-4 | Pr | H | 2,4-Cl₂ | H | 2-Me | |
| 2-5 | Pr | H | 2,4-Cl₂ | H | 2,3-(Me)₂ | |
| 2-6 | Pr | H | 2,4-Cl₂ | H | 2-OMe, 5-Me | |
| 2-7 | Pr | H | 2,4-Cl₂ | H | 2-OMe, 5-Cl | |
| 2-8 | Pr | H | 2,4 Cl₂ | H | 2-NO2, 4-Cl | |
| 2-9 | Pr | H | 2,4-Cl₂ | Me | 2-OMe, 5-Me | |
| 2-10 | Pr | H | H | H | 2-OMe, 5-Me | |
| 2-11 | Pr | H | H | H | 2-OMe, 5-Cl | |
| 2-12 | Pr | H | H | H | 2-OMe | |
| 2-13 | Pr | H | H | H | 2,5-(Me)₂ | |
| 2-14 | Bu | H | 2,4-Cl₂ | H | 2,5-(Me)₂ | |
| 2-15 | Bu | H | 2,4-Cl₂ | H | 2-OMe, 5-Me | |
| 2-16 | Bu | H | 2,4-Cl₂ | H | 2-OMe, 5-Cl | |
| 2-17 | Bu | H | 2,4-Cl₂ | H | 2-NO₂, 4-Cl | |
| 2-18 | Bu | H | H | H | 2-OMe, 5-Me | |
| 2-19 | Bu | H | H | H | 2-OMe, 5-Cl | |
| 2-20 | Bu | H | H | H | 2-OMe | |
| 2-21 | Bu | H | H | H | 2,5-(Me)₂ | 202 |
| 2-22 | Me | H | 4-Cl | H | 2-Cl | |
| 2-23 | Me | H | 4-Cl | H | 2-Me | 204 |
| 2-24 | Me | H | 4-Cl | H | 2,3-(Me)₂ | 215 |
| 2-25 | Me | Me | 2,4-Cl₂ | H | 2-OMe, 5-Me | |
| 2-26 | Me | Me | 2,4-Cl₂ | H | 2-OMe, 5-Cl | |
| 2-27 | Me | Me | 2,4-Cl₂ | H | 2-NO₂, 4-Cl | |
| 2-28 | Me | Me | 4-Cl | H | 2-OMe, 5-Me | |
| 2-29 | Me | Me | 4-Cl | H | 2-OMe, 5-Cl | |
| 2-30 | Me | Me | 4-Cl | H | 2-NO2, 4-Cl | |
| 2-31 | Me | Me | 4-Cl | Me | 2-OMe, 5-Me | |
| 2-32 | Me | Me | H | H | 2-OMe, 5-Me | |

TABLE 2-continued

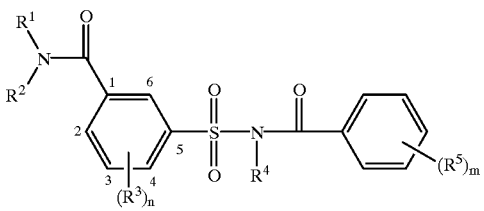

| No. | R¹ | R² | R³ | R⁴ | R⁵ | m.p [° C.] |
|---|---|---|---|---|---|---|
| 2-33 | Me | Me | H | H | 2-OMe, 5-Cl | resin |
| 2-34 | Me | Me | H | H | 2-NO₂, 4-Cl | |
| 2-35 | Me | Me | H | H | 2-OMe | 202 |
| 2-36 | C₂H₄— | H | 2,4-Cl₂ | H | 2-OMe | 177 |
| 2-37 | C₂H₄— | H | 2,4-Cl₂ | H | 2-Me | 180 |
| 2-38 | C₂H₄— | H | 2,4-Cl₂ | H | 2,5-(Me)₂ | |
| 2-39 | C₂H₄— | H | 2,4-Cl₂ | H | 2-Cl | 181 |
| 2-40 | C₂H₄— | H | 2,4-Cl₂ | H | 2,5-Cl₂ | 203 |
| 2-41 | c-Pr | H | 2,4-Cl₂ | H | 2,5-(Me)₂ | 264 |
| 2-42 | c-Pr | H | 2,4-Cl₂ | H | 2-OMe | 174 |
| 2-43 | c-Pr | H | 2,4-Cl₂ | H | 2-Cl | 214 |
| 2-44 | c-Pr | H | 2,4-Cl₂ | H | 2-Me | |
| 2-45 | c-Pr | H | 4-Cl | H | 2-OMe | 180 |
| 2-46 | c-Pr | H | 4-Cl | H | 2-Me | 250 |
| 2-47 | c-Pr | H | 2,4-Cl₂ | H | 2,5-Cl₂ | 233 |
| 2-48 | c-Pr | H | 2,4-Cl₂ | H | 2,3-(Me)₂ | |
| 2-49 | c-Pr | H | 2,4-Cl₂ | H | 2-OMe, 5-Me | |
| 2-50 | c-Pr | H | 2,4-Cl₂ | H | 2-OMe, 5-Cl | |
| 2-51 | c-Pr | H | 2,4-Cl₂ | H | 2-NO₂, 4-Cl | |
| 2-52 | c-Pr | H | 4-Cl | H | 2-Cl | 222 |
| 2-53 | c-Pr | H | 4-Cl | H | 2,5-(Me)₂ | |
| 2-54 | c-Pr | H | 4-Cl | H | 2-OMe, 5-Me | |
| 2-55 | c-Pr | H | 4-Cl | H | 2-OMe, 5-Cl | |
| 2-56 | c-Pr | H | 4-Cl | H | 2-NO2, 4-Cl | |
| 2-57 | c-Pr | H | 4-Cl | Me | 2-OMe, 5-Me | |
| 2-58 | c-Pr | H | H | H | 2,5-(Me)₂ | |
| 2-59 | c-Pr | H | H | H | 2-OMe, 5-Me | |
| 2-60 | c-Pr | H | H | H | 2-OMe, 5-Cl | |
| 2-61 | c-Pr | H | H | H | 2-NO₂, 4-Cl | |
| 2-62 | allyl | H | 2,4-Cl₂ | H | 2-OMe | 188 |
| 2-63 | allyl | H | 2,4-Cl₂ | H | 2-Cl | 147 |
| 2-64 | allyl | H | 2,4-Cl₂ | H | 2-Me | |
| 2-65 | allyl | H | 2,4-Cl₂ | H | 2,5-(Me)₂ | |
| 2-66 | allyl | H | 2,4-Cl₂ | H | 2,5-Cl₂ | 90 |
| 2-67 | CH₂C≡C | H | 2,4-Cl₂ | H | 2,5-(Me)₂ | |
| 2-68 | CH₂C≡C | H | 2,4-Cl₂ | H | 2-OMe, 5-Me | |
| 2-69 | CH₂C≡C | H | 2,4-Cl₂ | H | 2-OMe, 5-Cl | |
| 2-70 | CH₂C≡C | H | 2,4-Cl₂ | H | 2-NO₂, 4-Cl | |
| 2-71 | CH₂C≡C | H | 2,4-Cl₂ | Me | 2-OMe, 5-Me | |
| 2-72 | CH₂C≡C | H | 4-Cl | H | 2,5-(Me)₂ | |
| 2-73 | CH₂C≡C | H | 4-Cl | H | 2-OMe, 5-Me | |
| 2-74 | CH₂C≡C | H | 4-Cl | H | 2-OMe, 5-Cl | |
| 2-75 | CH₂C≡C | H | 4-Cl | H | 2-NO₂, 4-Cl | |
| 2-76 | —(CH₂)₄— | | 2,4-Cl₂ | H | 2,5-(Me)₂ | |
| 2-77 | —(CH₂)₄— | | 2,4-Cl₂ | H | 2-OMe, 5-Me | |
| 2-78 | —(CH₂)₄— | | 2,4-Cl₂ | H | 2-OMe, 5-Cl | |
| 2-79 | —(CH₂)₄— | | 2,4-Cl₂ | H | 2-NO₂, 4-Cl | |
| 2-80 | —(CH₂)₄— | | 2,4-Cl₂ | Me | 2-OMe, 5-Me | |
| 2-81 | —(CH₂)₄— | | 4-Cl | H | 2,5-(Me)₂ | |
| 2-82 | —(CH₂)₄— | | 4-Cl | H | 2-OMe, 5-Me | |
| 2-83 | —(CH₂)₄— | | 4-Cl | H | 2-OMe, 5-Cl | |
| 2-84 | —(CH₂)₄— | | 4-Cl | H | 2-NO₂, 4-Cl | |
| 2-85 | —(CH₂)₄— | | 4-Cl | H | 2-OMe | |
| 2-86 | —(CH₂)₄— | | 4-Cl | H | 2-Cl | |
| 2-87 | —(CH₂)₄— | | 4-Cl | H | 2-Me | |
| 2-88 | —(CH₂)₄— | | H | H | 2-OMe, 5-Cl | 178 |
| 2-89 | —(CH₂)₄— | | H | H | 2-OMe | 154 |
| 2-90 | Me | Et | H | H | 2-OMe, 5-Cl | 82 |
| 2-91 | Me | Et | H | H | 2-OMe | 71 |
| 2-92 | c-Pr | H | H | H | 2-OMe | 185 |
| 2-93 | c-Pr | H | H | H | 2-OMe | 183 |
| 2-94 | c-Pr | H | H | H | 2,5-(Me)₂ | 216 |
| 2-95 | i-Pr | H | H | H | 2-OMe | 179 |
| 2-96 | i-Pr | H | H | H | 2,5-(Me)₂ | 178 |
| 2-97 | Me | H | H | H | 2-OMe | 117 |
| 2-98 | Me | H | H | H | 2,5-(Me)₂ | 156 |

TABLE 3

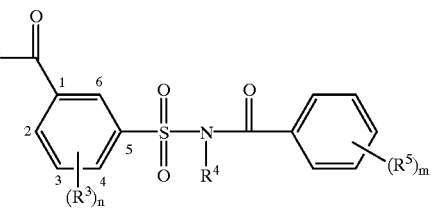

| No. | R¹ | R² | R³ | R⁴ | R⁵ | m.p [° C.] |
|---|---|---|---|---|---|---|
| 3-1 | Pr | H | H | H | 2,5-(Me)₂ | |
| 3-2 | Pr | H | H | H | 2-OMe | |
| 3-3 | Pr | H | H | H | 2-Cl | |
| 3-4 | Pr | H | H | H | 2-Me | |
| 3-5 | Pr | H | H | H | 2,3-(Me)₂ | |
| 3-6 | Pr | H | H | H | 2-OMe, 5-Me | |
| 3-7 | Pr | H | H | H | 2-OMe, 5-Cl | |
| 3-8 | Pr | H | H | H | 2-NO₂, 4-Cl | |
| 3-9 | Pr | H | H | Me | 2-OMe, 5-Me | |
| 3-10 | Pr | H | 2-Cl | H | 2-OMe, 5-Me | |
| 3-11 | Pr | H | 2-Cl | H | 2-OMe, 5-Cl | |
| 3-12 | Pr | H | 2-Cl | H | 2-OMe | |
| 3-13 | Pr | H | 2-Cl | H | 2,5-(Me)₂ | |
| 3-14 | Bu | H | H | H | 2,5-(Me)₂ | |
| 3-15 | Bu | H | H | H | 2-OMe, 5-Me | |
| 3-16 | Bu | H | H | H | 2-OMe, 5-Cl | |
| 3-17 | Bu | H | H | H | 2-NO₂, 4-Cl | |
| 3-18 | Bu | H | 2-Cl | H | 2-OMe, 5-Me | |
| 3-19 | Bu | H | 2-Cl | H | 2-OMe, 5-Cl | |
| 3-20 | Bu | H | 2-Cl | H | 2-OMe | |
| 3-21 | Bu | H | 2-Cl | H | 2,5-(Me)₂ | |
| 3-22 | Me | H | 2-Cl | H | 2-Cl | |
| 3-23 | Me | H | 2-Cl | H | 2-Me | |
| 3-24 | Me | H | 2-Cl | H | 2,3-(Me)₂ | |
| 3-25 | Me | Me | H | H | 2-OMe, 5-Me | |
| 3-26 | Me | Me | H | H | 2-OMe, 5-Cl | |
| 3-27 | Me | Me | H | H | 2-NO₂, 4-Cl | |
| 3-28 | Me | Me | 2-Cl | H | 2-OMe, 5-Me | |
| 3-29 | Me | Me | 2-Cl | H | 2-OMe, 5-Cl | |
| 3-30 | Me | Me | 2-Cl | H | 2-NO2, 4-Cl | |
| 3-31 | Me | Me | 2-Cl | Me | 2-OMe, 5-Me | |
| 3-32 | Me | Me | 4-NO₂ | H | 2-OMe, 5-Me | |
| 3-33 | Me | Me | 4-NO₂ | H | 2-OMe, 5-Cl | |
| 3-34 | Me | Me | 4-NO₂ | H | 2-NO₂, 4-Cl | |
| 3-35 | Me | Me | 4-NO₂ | H | 2-OMe | |
| 3-36 | C₂H₄—OMe | H | H | H | 2-OMe | |
| 3-37 | C₂H₄—OMe | H | H | H | 2-Me | |
| 3-38 | C₂H₄—OMe | H | H | H | 2,5-(Me)₂ | |
| 3-39 | C₂H₄—OMe | H | H | H | 2-Cl | |
| 3-40 | C₂H₄—OMe | H | H | H | 2,5-Cl₂ | |
| 3-41 | c-Pr | H | H | H | 2,5-(Me)₂ | |
| 3-42 | c-Pr | H | H | H | 2-OMe | |

TABLE 3-continued

Structure with R¹, R², (R³)ₙ, R⁴, (R⁵)ₘ on benzamide-sulfonyl-benzamide scaffold

| No. | R¹ | R² | R³ | R⁴ | R⁵ | m.p. [° C.] |
|---|---|---|---|---|---|---|
| 3-43 | c-Pr | H | H | H | 2-Cl | |
| 3-44 | c-Pr | H | H | H | 2-Me | |
| 3-45 | c-Pr | H | 2-Cl | H | 2-OMe | |
| 3-46 | c-Pr | H | 2-Cl | H | 2-Me | |
| 3-47 | c-Pr | H | 2-Cl | H | 2-Cl | |
| 3-48 | c-Pr | H | 2-Cl | H | 2,5-(Me)₂ | |
| 3-49 | c-Pr | H | 2-Cl | H | 2-OMe, 5-Me | |
| 3-50 | c-Pr | H | 2-Cl | H | 2-OMe, 5-Cl | |
| 3-51 | c-Pr | H | 2-Cl | H | 2-NO₂, 4-Cl | |
| 3-52 | c-Pr | H | 2-Cl | Me | 2-OMe, 5-Me | |
| 3-53 | allyl | H | H | H | 2-OMe | |
| 3-54 | allyl | H | H | H | 2-Cl | |
| 3-55 | allyl | H | H | H | 2-Me | |
| 3-56 | allyl | H | H | H | 2,5-(Me)₂ | |
| 3-57 | allyl | H | H | H | 2,5-Cl₂ | |
| 3-58 | CH₂C≡CH | H | H | H | 2,5-(Me)₂ | |
| 3-59 | CH₂C≡CH | H | H | H | 2-OMe, 5-Me | |
| 3-60 | CH₂C≡CH | H | H | H | 2-OMe, 5-Cl | |
| 3-61 | CH₂C≡CH | H | H | H | 2-NO₂, 4-Cl | |
| 3-62 | CH₂C≡CH | H | H | Me | 2-OMe, 5-Me | |

TABLE 4

Structure with R¹, R², (R³)ₙ, R⁴, (R⁵)ₘ on benzamide-sulfonyl-pyridine carbonyl scaffold

| No. | Compound | m.p. [° C.] |
|---|---|---|
| 4-1 | 4-(2-methoxypyridin-3-ylcarbonylsulfamoyl)-N-propylbenzamide | |
| 4-2 | 3-(2-methoxypyridin-3-ylcarbonylsulfamoyl)-N-propylbenzamide | |
| 4-3 | N-isopropyl-4-(2-methoxypyridin-3-ylcarbonylsulfamoyl)benzamide | 230 |
| 4-4 | N-isopropyl-4-(2-methylthiopyridin-3-ylcarbonylsulfamoyl)benzamide | |
| 4-5 | N-isopropyl-4-(2-methylpyridin-3-ylcarbonylsulfamoyl)benzamide | |
| 4-6 | N-isopropyl-4-(4-trifluoromethylpyridin-3-ylcarbonylsulfamoyl)benzamide | |
| 4-7 | N-cyclopropyl-4-(2-methoxypyridin-3-ylcarbonylsulfamoyl)benzamide | 230 |
| 4-8 | N-cyclopropyl-3-nitro-4-(2-methoxypyridin-3-ylcarbonylsulfamoyl)benzamide | |
| 4-9 | N-cyclopropyl-4-(2-methylthiopyridin-3-ylcarbonylsulfamoyl)benzamide | |
| 4-10 | N-cyclopropyl-4-(2-methylpyridin-3-ylcarbonylsulfamoyl)benzamide | |
| 4-11 | N-cyclopropyl-4-(4-trifluoromethylpyridin-3-ylcarbonylsulfamoyl)benzamide | |
| 4-12 | N-cyclopropyl-4-(2-chloro-6-methylpyridin-3-ylcarbonylsulfamoyl)benzamide | |
| 4-13 | N-(1,2-dimethylpropyl)-4-(2-methoxypyridin-3-ylcarbonylsulfamoyl)benzamide | 206 |
| 4-14 | 4-(2-methoxypyridin-3-ylcarbonylsulfamoyl)-N-(2-phenylethyl)benzamide | |
| 4-15 | 2,4-dichloro-N-cyclopropyl-5-(2-methoxypyridin-3-ylcarbonylsulfamoyl)benzamide | 224 |
| 4-16 | 4-chloro-N-cyclopropyl-3-(2-methoxypyridin-3-ylcarbonylsulfamoyl)benzamide | 185 |
| 4-17 | N-cyclopropyl-3-(2-methoxypyridin-3-ylcarbonylsulfamoyl)benzamide | |
| 4-18 | N-cyclopropyl-2-(2-methoxypyridin-3-ylcarbonylsulfamoyl)benzamide | |
| 4-19 | 4-(2-methoxypyridin-3-ylcarbonylsulfamoyl)-N-methylbenzamide | |
| 4-20 | N-ethyl-4-(2-methoxypyridin-3-ylcarbonylsulfamoyl)benzamide | |
| 4-21 | 2,4-dichloro-5-(2-methoxypyridin-3-ylcarbonyl-sulfamoyl)-N-propylbenzamide | |
| 4-22 | 4-chloro-3-(2-methoxypyridin-3-ylcarbonylsulfamoyl)-N-propylbenzamide | |
| 4-23 | N,N-dimethyl-4-(2-methoxypyridin-3-ylcarbonylsulfamoyl)benzamide | |
| 4-24 | N-allyl-4-(2-methoxypyridin-3-ylcarbonylsulfamoyl)benzamide | |
| 4-25 | 4-(2-methoxypyridin-3-ylcarbonylsulfamoyl)-N-propargylbenzamide | |
| 4-26 | 2,4-dichloro-N-ethyl-5-(2-methoxypyridin-3-ylcarbonylsulfamoyl)benzamide | |
| 4-27 | 4-chloro-N-ethyl-3-(2-methoxypyridin-3-ylcarbonylsulfamoyl)benzamide | |
| 4-28 | 2,4-dichloro-5-(2-methoxypyridin-3-ylcarbonyl-sulfamoyl)-N-methylbenzamide | |
| 4-29 | 4-chloro-3-(2-methoxypyridin-3-ylcarbonylsulfamoyl)-N-methylbenzamide | |

What is claimed is:

1. A crop protection composition comprising one or more pesticides, and at least one acylsulfamoylbenzamide of the formula

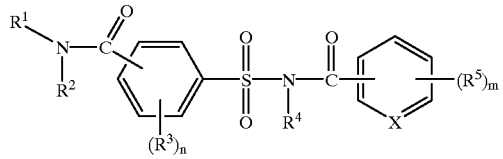

(I)

or, its salt, in which

X is CH or N;

R¹ is hydrogen, heterocyclyl or a hydrocarbon radical, where the two last mentioned radicals are optionally substituted by one or more identical or different radicals selected from the group consisting of halogen, cyano, nitro, amino, hydroxyl, carboxyl, CHO, $CONH_2$, $SO_2NH_2$ and $Z^a$—$R^a$;

R² is hydrogen, hydroxyl, $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, where the five last-mentioned radicals are optionally substituted by one or more identical or different radicals selected from the group consisting of halogen, hydroxyl, $(C_1-C_4)$-alkyl, $(C_1-C_4)$-alkoxy and $(C_1-C_4)$-alkylthio, or $R^1$ and $R^2$ together with the linking nitrogen atom form a 3- to 8-membered saturated or unsaturated ring;

$R^3$ is halogen, cyano, nitro, amino, hydroxyl, carboxyl, CHO, $CONH_2$, $SO_2NH_2$ or $Z^b$—$R^b$;

$R^4$ is hydrogen, $(C_1-C_4)$-alkyl, $(C_2-C_4)$-alkenyl or $(C_2-C_4)$-alkynyl;

$R^5$ is halogen, cyano, nitro, amino, hydroxyl, carboxyl, phosphnoryl, CHO, $CONH_2$, $SO_2NH_2$ or $Z^c$—$R^c$;

$R^a$ is a $(C_2-C_{20})$-alkyl radical whose hydrocarbon chain is interrupted once or more than once by oxygen atoms, is heterocyclyl or a hydrocarbon radical, where the two last-mentioned radicals are optionally substituted by one or more identical or different radicals selected from the group consisting of halogen, cyano, nitro, amino, hydroxyl, alkylthio, mono- and di-$((C_1-C_4)$-alkyl)amino;

$R^b$, $R^c$ independently of one another are a $(C_2-C_{20})$-alkyl radical whose hydrocarbon chain is interrupted once or more than once by oxygen atoms, are heterocyclyl or a hydrocarbon radical, where the two last-mentioned radicals are optionally substituted by one or more identical or different radicals selected from the group consisting of halogen, cyano, nitro, amino, hydroxyl, phosphoryl, $(C_1-C_4)$-haloalkoxy, mono- and di-$((C_1-C_4)$-alkyl)amino;

$Z^a$ is a divalent unit selected from the group consisting of O, S, CO, CS, C(O)O, C(O)S, SO, $SO_2$, $N^{Rd}$ or $SO_2NR^d$;

$Z^b$, $Z^c$ independently of one another are a direct bond or a divalent unit selected from the group consisting of O, S, CO, CS, C(O)O, C(O)S, SO, $SO_2$, $NR^d$, $SO_2NR^d$ or $C(O)NR^d$;

$R^d$ is hydrogen, $(C_1-C_4)$-alkyl or $(C_1-C_4)$-haloalkyl;

n is an integer from 0 to 4 and m, in the case that X is CH, is an integer from 0 to 5, and, in the case that X is N, is an integer from 0 to 4.

2. The crop protection composition as claimed in claim 1, wherein $R^1$ is hydrogen, 3- to 8-membered heterocyclyl having one to three identical or different hetero-atoms selected from the group consisting of nitrogen, oxygen and sulfur, $(C_1-C_{12})$-alkyl, $(C_2-C_8)$-alkenyl, $(C_2-C_8)$-alkynyl, $(C_3-C_8)$-cycloalkyl, $(C_3-C_8)$-cycloalkenyl or aryl, where the seven last-mentioned radicals are optionally substituted by one or more identical or different radicals selected from the group consisting of halogen, cyano, nitro, amino, hydroxyl, carboxyl, CHO, $CONH_2$ or $Z^c$—$R^c$;

$R^a$ is a $(C_2-C_{12})$-alkyl radical whose hydrocarbon chain is interrupted once or more than once by oxygen atoms, is $(C_1-C_8)$-alkyl, $(C_3-C_6)$-cycloalkyl, $(C_2-C_8)$-alkenyl, $(C_3-C_6)$-cycloalkenyl, $(C_2-C_8)$-alkynyl, phenyl or 3- to 6-membered heterocyclyl having one to three identical or different hetero-atoms selected from the group consisting of nitrogen, oxygen and sulfur, where the seven last-mentioned radicals independently of one another are optionally substituted by one or more nitro, amino, hydroxyl, mono- and di-$((C_1-C_4)$-alkyl)amino;

$R^b$, $R^c$ independently of one another are a $(C_2-C_{12})$-alkyl radical whose hydrocarbon chain is interrupted once or more than once by oxygen atoms, is $(C_1-C_8)$-alkyl, $(C_3-C_6)$-cycloalkyl, $(C_2-C_8)$-alkenyl, $(C_3-C_6)$-cycloalkenyl, $(C_2-C_8)$-alkynyl, phenyl or 3- to 6-membered heterocyclyl having one to three identical or different hetero atoms selected from the group consisting of N, O and S, where the seven last mentioned radicals independently of one another are optionally substituted by one or more identical or different radicals selected from the group consisting of halogen, cyano, nitro, amino, hydroxyl, phosphoryl, $(C_1-C_4)$-haloalkoxy, mono and di$((C_1-C_4)$-alkyl)amino;

$Z^a$ is a divalent unit selected from the group consisting of O, S, CO, CS, C(O)O, C(O)S, SO, $SO_2$, $NR^d$ or $C(O)NR^d$;

$Z^b$, $Z^c$ independently of one another are a direct bond or a divalent unit selected from the group consisting of O, S, CO, CS, C(O)O, C(O)S, SO, $SO_2$, $NR^d$ or $C(O)NR^d$ and $R^d$ is hydrogen, $(C_1-C_4)$-alkyl or $(C_1-C_4)$-haloalkyl.

3. The crop protection composition as claimed in claim 1, wherein $R^1$ is hydrogen, $(C_1-C_8)$-alkyl, $(C_2-C_6)$-alkenyl, $(C_2-C_6)$-alkynyl, $(C_3-C_6)$-cycoloalkyl, $(C_5-C_6)$-cycloalkenyl, phenyl or 3- 6-membered heteocyclyl having one to three hetero atoms selected from the group consisting of nitrogen, oxygen and sulfur, where the seven last-mentioned radicals are optionally substituted by one or more identical or different substituents selected from the group consisting of halogen, cyano, $(C_1-C_6)$-alkoxy, $(C_1-C_6)$-alkylthio, $(C_1-C_4)$-alkylsulfinyl, $(C_1-C_4)$-alkylsulfonyl, $(C_2-C_4)$-alkenyloxy, $(C_2-C_4)$-alkenylthio, $(C_2-C_4)$-alkynyloxy, $(C_2-C_4)$-alkynylthio, $(C_3-C_6)$-cycloalkyl, $(C_5-C_6)$-cycloalkenyl, $(C_3-C_6)$-cycloalkoxy, $(C_5-C_6)$-cycloalkenyloxy, mono and di-$((C_1-C_4)$-alkyl)amino, $((C_1-C_6)$-alkoxy)carbonyl, $((C_1-C_6)$-alkyl)carbonyl, phenyl, phenyl-$(C_1-C_4)$-alkoxy, 5- to 6-membered heterocyclyl having one to three hetero atoms selected from the group consisting of nitrogen, oxygen and sulfur and, in the case of cyclic radicals, also by $(C_1-C_4)$-alkyl, where the twenty last-mentioned radicals are optionally substituted by one or more identical or different substituents selected form the group consisting of halogen and cyano and, in the case of cyclic radicals, also by $(C_1-C_4)$-alkyl; $R^3$, $R^5$ independently of one another are halogen, nitro, amino, hydroxyl, cyano, $SO_2NH_2$, $(C_1-C_6)$-alkyl, $(C_3-C_6)$-cycloalkyl, $(C_2-C_6)$-alkenyl, $(C_2-C_6)$-alkynyl, $(C_1-C_6)$-alkoxy, $(C_2-C_6)$-alkenyloxy, $(C_2-C_6)$-alkynyloxy, mono- and di$((C_1-C_4)$-alkyl)-aminosulfonyl, $(C_1-C_6)$-alkylthio, $(C_1-C_6)$-alkylsulfinyl, $(C_1-C_6)$-alkylsulfonyl, $(C_1-C_6)$-alkoxycarbonyl, $(C_1-C_6)$-alkylthiocarbonyl, $(C_1-C_6)$-alkylcarbonyl, where the fifteen last-mentioned radicals are optionally substituted by one or more identical or different radicals selected from the group consisting of halogen, $(C_1-C_4)$-haloalkoxy, cyano, $(C_1-C_6)$-alkoxy and, in the case of cyclic radicals, also by $(C_1-C_4)$-alkyl and $(C_1-C_4)$-haloalkyl.

4. The crop protection composition as claimed in claim 1, wherein

X is CH, $R^1$ is hydrogen, $(C_1-C_6)$-alkyl, $(C_3-C_6)$-cycloalkyl, $(C_2-C_6)$-alkenyl, $(C_5-C_6)$-cycloalkenyl, phenyl or 3- to 6-membered heterocyclyl having one to three hetero-atoms selected from the group consisting of nitrogen, oxygen and sulfur, where the six last mentioned radicals are optionally substituted by one or more identical different substituents selected from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also by $(C_1-C_4)$-alkyl and $(C_1-C_4)$-haloalkyl;

$R^2$ is hydrogen, $(C_1-C_6)$-alkyl, $(C_2-C_6)$-alkenyl, $(C_2-C_6)$-alkynyl, where the three last mentioned radicals are optionally substituted by one or more identical or different substituents selected from the group consisting of halogen, hydroxyl, $(C_1-C_4)$-alkyl, $(C_1-C_4)$-alkoxy and $(C_1-C_4)$-alkylthio;

$R^3$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;

$R^4$ is hydrogen;

$R^5$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$- alkoxy, cyano, $(C_1–C_4)$-alkylthio, $(C_1–C_4)$-alkylsulfinyl, $(C_1–C_4)$-alkylsulfonyl, $(C_1–C_4)$-alkoxycarbonyl or $(C_1–C_4)$-alkylcarbonyl;

n is 0, 1 or 2 and m is 1 or 2.

5. A crop protection composition of claim 1, wherein $R^1$ is hydrogen, $(C_1–C_6)$-alkyl, $(C_3–C_6)$-cycloalkyl, where the two last mentioned radicals are optionally substituted by one or more identical or different substituents selected from the group consisting of halogen, $(C_1–C_4)$-alkoxy, $(C_1–C_6)$-haloalkoxy and $(C_1–C_4)$-alkylthio and, in the case of cyclic radicals, also by $(C_1–C_4)$-alkyl and $(C_1–C_4)$-haloalkyl.

6. The crop protection composition of claim 1, wherein the sulfamoyl group is in position 4 of the phenyl ring.

7. The crop protection composition of claim 1, wherein the pesticide is a herbicide.

8. The crop protection composition as claimed in claim 7, where the herbicide is selected from the groups A) Phenoxyphenoxy- and heteroaryloxyphenoxycarboxylic acid derivatives B) Sulfonylureas C) Chloroacetanilides D) Thiocarbamates E) Cyclohexanedione oximes F) Imidazolinones G) Triazolopyrimidinesulfonamide derivatives H) Benzoylcyclohexanediones I) Pyrimidinyloxypyridinecarboxylic acid or pyrimidinyloxybenzoic acid derivatives and J) S-(N-aryl-N-alkylcarbamoylmethyl)dithiophosphonic esters.

9. A method for protecting useful plants against the phytotoxic properties of pesticides, which comprises applying a crop protection composition as claimed in claim 1, to a crop of useful plants or to an environment where the crop plants will or do reside.

10. An acylsulfamoylbenzamide compound having the formula I:

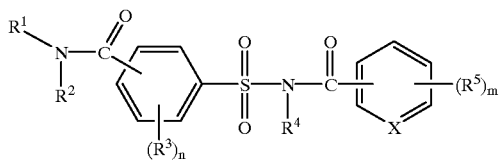

(I)

or, its salt, in which

X is CH or N;

$R^1$ is hydrogen, heterocyclyl or a hydrocarbon radical, where the two last mentioned radicals are optionally substituted by one or more identical or different radicals selected from the group consisting of halogen, cyano, nitro, amino, hydroxyl, carboxyl, CHO, $CONH_2$, $SO_2NH_2$ and $Z^a$—$R^a$;

$R^2$ is hydrogen, hydroxyl, $(C_1–C_6)$-alkyl, $(C_2–C_6)$-alkenyl, $(C_2–C_6)$-alkynyl, $(C_1–C_6)$-alkoxy, $(C_2–C_6)$-alkenyloxy, where the five last-mentioned radicals are optionally substituted by one or more identical or different radicals selected from the group consisting of halogen, hydroxyl, $(C_1–C_4)$-alkyl, $(C_1–C_4)$-alkoxy and $(C_1–C_4)$-alkylthio, or $R^1$ and $R^2$ together with the linking nitrogen atom form a 3- to 8-membered saturated or unsaturated ring;

$R^3$ is halogen, cyano, nitro, amino, hydroxyl, carboxyl, CHO, $CONH_2$, $SO_2NH_2$ or $Z^b$—$R^b$;

$R^4$ is hydrogen, $(C_1–C_4)$-alkyl, $(C_2–C_4)$-alkenyl or $(C_2–C_4)$-alkynyl;

$R^5$ is halogen, cyano, nitro, amino, hydroxyl, carboxyl, phosphoryl, CHO, $CONH_2$, $SO_2NH_2$ or $Z^c$—$R^c$;

$R^a$ is a $(C_2–C_{20})$-alkyl radical whose hydrocarbon chain is interrupted once or more than once by oxygen atoms, is heterocyclyl or a hydrocarbon radical, where the two last-mentioned radicals are optionally substituted by one or more identical or different radicals selected from the group consisting of halogen, cyano, nitro, amino, hydroxyl, mono- and di-(($C_1–C_4$)-alkyl)amino; $R^b$, $R^c$ independently of one another are a $(C_2–C_{20})$-alkyl radical whose hydrocarbon chain is interrupted once or more than once by oxygen atoms, are heterocyclyl or a hydrocarbon radical, where the two last-mentioned radicals are optionally substituted by one or more identical or different radicals selected from the group consisting of halogen, cyano, nitro, anino, hydroxyl, phosphoryl, $(C_1–C_4)$-haloalkoxy, mono- and di-(($C_1–C_4$)-alkyl)amino;

$Z^a$ is a divalent unit selected from the group consisting of O, S, CO, CS, C(O)O, C(O)S, SO, $SO_2$, $NR^d$ or $SO_2NR^d$;

$Z^b$, $Z^c$ independently of one another are a direct bond or a divalent unit selected from the group consisting of O, S, CO, CS, C(O)O, C(O)S, SO, $SO_2$, $NR^d$, $SO_2NR^d$ or $C(O)NR^d$;

$R^d$ is hydrogen, $(C_1–C_4)$-alkyl or $(C_1–C_4)$-haloalkyl;

n is an integer from 0 to 4 and m, in the case that X is CH, is an integer from 0 to 5, and, in the case that X is N, is an integer from 0 to 4; with the proviso that $R^5$ is not attached directly adjacent to X if X is N and that $R^1$ is not phenyl, benzyl or 4-carboxyphenyl if X is CH and $R^2$, $R^4$ and $R^5$ are each hydrogen.

11. A method for protecting useful plants against phytotoxic properties of pesticides, which comprises applying a crop protection composition comprising the acylsulfamoylbenzamide compound as claimed in claim 10 to a crop of useful plants or to an environment where the crop plants will or do reside.

12. A process for preparing acylsulfamoylbenzamides as claimed in claim 10 which comprises a) reacting a compound of the formula II

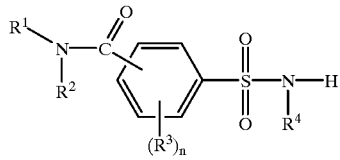

(II)

with an acylating agent of the formula III

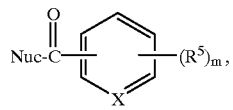 (III)

where Nuc is a leaving group, or reacting a carboxylic acid directly with the sulfonamide of the formula II by employing coupling agents, or b) reacting a compound of the formula IV

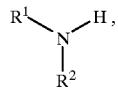 (IV)

with activated carboxylic acid derivatives of the formula V

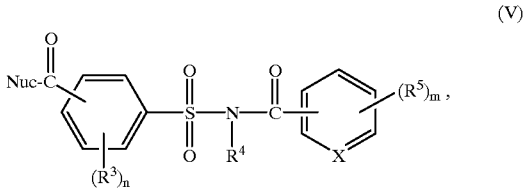 (V)

where Nuc is a leaving group.

13. The process of claim 12, wherein the coupling agents comprise dicyclohexylcarbodiimide.

14. The process of claim 12 wherein the coupling agent is dicyclohexylcarbodiimide.

* * * * *